United States Patent
Dai et al.

(10) Patent No.: US 12,213,911 B1
(45) Date of Patent: *Feb. 4, 2025

(54) PORTABLE SYSTEM AND DEVICE FOR COLD THERAPY WITH OPTIONAL HEAT AND COMPRESSION THERAPY

(71) Applicants: Quanqin Dai, Shenzhen (CN); Pu Jiang, Shenzhen (CN)

(72) Inventors: Quanqin Dai, Shenzhen (CN); Pu Jiang, Shenzhen (CN)

(73) Assignee: JKH USA, LLC, Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/766,548

(22) Filed: Jul. 8, 2024

Related U.S. Application Data

(63) Continuation-in-part of application No. 18/386,568, filed on Nov. 2, 2023, now Pat. No. 12,070,413.

(30) Foreign Application Priority Data

Sep. 8, 2023 (CN) .......................... 202322449198.9

(51) Int. Cl.
  *A61F 7/03* (2006.01)
  *A61F 7/00* (2006.01)
  *A61F 7/02* (2006.01)
  *F25B 13/00* (2006.01)

(52) U.S. Cl.
  CPC .............. *A61F 7/02* (2013.01); *A61F 7/0085* (2013.01); *A61F 2007/0056* (2013.01); *F25B 13/00* (2013.01)

(58) Field of Classification Search
  CPC .. A61F 7/03; A61F 7/0085; A61F 2007/0055; A61F 2007/0056; A61F 2007/0087
  See application file for complete search history.

(56) References Cited

U.S. PATENT DOCUMENTS

| | | | |
|---|---|---|---|
| 6,878,156 B1 | 4/2005 | Noda | |
| 2006/0235496 A1* | 10/2006 | Collins | A61F 7/12 607/113 |
| 2017/0219261 A1 | 8/2017 | Mahrouche et al. | |
| 2020/0000628 A1* | 1/2020 | Lowe | A61F 7/00 |
| 2023/0414444 A1 | 12/2023 | Sundar et al. | |

* cited by examiner

*Primary Examiner* — Tigist S Demie
(74) *Attorney, Agent, or Firm* — Arch & Lake LLP; Hao Tan; Shen Wang

(57) ABSTRACT

A portable system for cold therapy with optional heat and compression therapy is disclosed, including a cooling mechanism, a reservoir, and a control assembly. The cooling mechanism includes a compressor, a condenser, a fan, and a heat exchanger. The compressor has an air inlet connected to the heat exchanger through a first tube. The heat exchanger is connected to the condenser through a second tube. The condenser is connected to an air outlet of the compressor through a third tube. The first tube and the second tube are connected by fluid, and the second tube and the third tube are connected by fluid. The fan has a working surface facing the condenser. The liquid in the reservoir flows into the heat exchanger and then flows into the first body wrap, and then can flow into the heat exchanger or flow back into the reservoir.

24 Claims, 19 Drawing Sheets

PORTABLE SYSTEM AND DEVICE FOR COLD THERAPY WITH OPTIONAL HEAT AND COMPRESSION THERAPY

CROSS REFERENCE TO RELATED APPLICATIONS

This present application claims the benefit of, and is a continuation-in-part of U.S. Non-Provisional patent application Ser. No. 18/386,568, filed on Nov. 2, 2023, which claims priority to Chinese Application No. CN202322449198.9, filed on Sep. 8, 2023, the disclosure of which is incorporated herein by reference in its entirety for all purposes.

TECHNICAL FIELD

The various embodiments described in this document relate in general to the field of medical devices, and more particularly, to a portable system and device for cold therapy with optional heat and compression therapy.

BACKGROUND

The cold therapy system and device (e.g., body wraps) are widely used in medical fields such as exercise rehabilitation, pain relief, swelling elimination, wound healing and the like.

A conventional cold therapy system and device are mainly utilizes a semiconductor for cooling, while using the semiconductor for cooling has the following deficiencies.

1. When using the semiconductor for cooling, temperature controllability of system and device (e.g., body wraps) are limited, and improper temperature control may result in excessive heat loss of a chip and even loss of cooling effect.

2. Cooling effect of the semiconductor is easily affected by ambient temperature. When the ambient temperature exceeds a specific range, it is difficult to effectively absorb heat, resulting in a decrease in cooling effect.

3. The use of the semiconductor for cooling is generally to fix a refrigeration chip on a cooling fin and control operation of the chip by means of current to take away heat. When the current passes through the chip, an N-type semiconductor absorbs surrounding heat and a P-type semiconductor releases heat, which causes one side of the chip to be in a low-temperature state and the other side to be in a high-temperature state. By connecting a water tube, water flows through a low-temperature surface of the chip, so that the cooling is driven by using electric energy. This method causes excessively large power consumption and relatively large size of the device, and commercial power is required to supply power, which is difficult to use in an environment without the commercial power or away from the commercial power and is inconvenient to carry out for use.

Moreover, conventional cold therapy devices offer a limited functionality and inconvenience in adapting to diverse scenarios.

Therefore, it is desired to find an adaptable cooling system and cooling therapy device.

SUMMARY

With respect to the technical problems of insufficient cooling effect and low efficiency in cooling mechanism of conventional cold therapy devices, embodiments of the present disclosure aim to provide a portable system and device for cold therapy with optional heat and compression therapy, which enhances efficiency and stability of the cooling, reduces power consumption, has a compact and lightweight structure, offers various functionality, and improves user's experience.

According to a first aspect, embodiments of the present disclosure provide a portable system for cold therapy with optional heat and compression therapy, applied to a first body wrap, including a cooling mechanism, a reservoir, and a control assembly; wherein the cooling mechanism comprises a compressor, a condenser, a fan, and a heat exchanger, and the control assembly is electrically connected to the compressor, the condenser, and the fan, respectively; and wherein: the compressor, the condenser, and the fan are placed outside the reservoir; the heat exchanger is placed inside or underneath the reservoir, and is in direct or indirect contact with liquid in the reservoir to cool the liquid; the compressor has an air inlet connected to the heat exchanger through a first tube; the heat exchanger is connected to the condenser through a second tube; the condenser is connected to an air outlet of the compressor through a third tube; the first tube and the second tube are connected by fluid, and the second tube and the third tube are connected by fluid, enabling refrigerant in the compressor to pass through the condenser first and then through the heat exchanger to achieve a cooling effect; the fan has a working surface facing the condenser. The reservoir comprises a first liquid inlet of the reservoir and a first liquid outlet of the reservoir; wherein the liquid in the reservoir flows into the first body wrap through the first liquid outlet of the reservoir, and liquid in the first body wrap flows into the reservoir through the first liquid inlet of the reservoir; the heat exchanger comprises a first cooling plate placed inside the reservoir; wherein the first cooling plate comprises a first air inlet of the first cooling plate, a first air outlet of the first cooling plate, a second liquid inlet of the first cooling plate, and a second liquid outlet of the first cooling plate; and wherein the first air outlet of the first cooling plate is connected to the first tube, and the first air inlet of the first cooling plate is connected to the second tube; and the second liquid inlet of the first cooling plate is connected to the first liquid inlet of the reservoir through a fourth tube.

In accordance with the portable system for cold therapy with optional heat and compression therapy provided in the present disclosure, the advantageous effects include the following. The cooling mechanism is equipped with the compressor, the condenser, the fan, and the heat exchanger. High temperature and high-pressure refrigerant gas is transported from the compressor to the condenser through the third tube, at this time, the temperature of the refrigerant gas is high, and the fan is utilized to cool the refrigerant gas in the condenser, and the refrigerant gas is liquefied. Refrigerant liquid is transported from the condenser to the heat exchanger through the second tube. In the heat exchanger, the refrigerant liquid undergoes heat exchange with the liquid in the reservoir, absorbs heat from the liquid and gasifies, and the liquid temperature decreases. Refrigerant gas is transported from the heat exchanger to the compressor through the first tube, and the compressor compresses the refrigerant gas. This process circulates to cool the liquid in the reservoir, the liquid with decreased temperature flows into the first body wrap through the third liquid inlet, providing the first body wrap with a cold compression function. Under the condition of the ambient temperature of 25-28° C., with an area of 1 $m^2$ of the first body wrap, a cooling rate is such that the surface temperature of the first body wrap reaches 5° C. within about 10 minutes, a cooling power is about 75 watts, and the achieved cooling capacity is about 250 watts. The system exhibits excellent cooling effects, high efficiency, stability, and low power consumption. The device has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir, which are able to directly or indirectly contact the liquid in the reservoir. This allows pre-cooling or pre-heating of the liquid, thereby enabling immediate use when the user requires therapy.

According to a second aspect, embodiments of the present disclosure provide a portable system for cold therapy with optional heat and compression therapy, applied to a first body wrap, including a cooling mechanism, a reservoir, and a control assembly; wherein the cooling mechanism comprises a compressor, a condenser, a fan, and a heat exchanger, and the control assembly is electrically connected to the compressor, the condenser, and the fan, respectively; and wherein: the compressor, the condenser, and the fan are placed outside the reservoir; the heat exchanger is placed inside or underneath the reservoir, and is in direct or indirect contact with liquid in the reservoir to cool the liquid; the compressor has an air inlet connected to the heat exchanger through a first tube; the heat exchanger is connected to the condenser through a second tube; the condenser is connected to an air outlet of the compressor through a third tube; the first tube and the second tube are connected by fluid, and the second tube and the third tube are connected by fluid, enabling refrigerant in the compressor to pass through the condenser first and then through the heat exchanger to achieve a cooling effect; the fan has a working surface facing the condenser; and the reservoir comprises a first liquid inlet of the reservoir and a first liquid outlet of the reservoir; wherein the liquid in the reservoir flows into the first body wrap through the first liquid outlet of the reservoir, and liquid in the first body wrap flows into the reservoir through the first liquid inlet of the reservoir.

When the heat exchanger is placed inside the reservoir, the heat exchanger comprises a first cooling plate; wherein the first cooling plate comprises a first air inlet of the first cooling plate and a first air outlet of the first cooling plate; and wherein the first air outlet of the first cooling plate is connected to the first tube, and the first air inlet of the first cooling plate is connected to the second tube.

Or when the heat exchanger is placed inside the reservoir, the heat exchanger comprises a spiral tube; wherein the spiral tube has one end connected to the first tube and another end connected to the second tube.

When the heat exchanger is placed underneath the reservoir, the heat exchanger comprises a second cooling plate; wherein the second cooling plate is provided with a second air inlet of the second cooling plate and a second air outlet of the second cooling plate, the second air outlet of the second cooling plate is connected to the first tube, and the second air inlet of the second cooling plate is connected to the second tube; and wherein the reservoir comprises a heat-conducting material.

In accordance with the portable system for cold therapy with optional heat and compression therapy provided in the present disclosure, the advantageous effects include the following. In a first aspect, the cooling mechanism is equipped with the compressor, the condenser, the fan, and the heat exchanger. High temperature and high-pressure refrigerant gas is transported from the compressor to the condenser through the third tube, at this time, the temperature of the refrigerant gas is high, and the fan is utilized to cool the refrigerant gas in the condenser, and the refrigerant gas is liquefied. Refrigerant liquid is transported from the condenser to the heat exchanger through the second tube. In the heat exchanger, the refrigerant liquid undergoes heat exchange with the liquid in the reservoir, absorbs heat from the liquid and gasifies, and the liquid temperature decreases. Refrigerant gas is transported from the heat exchanger to the compressor through the first tube, and the compressor compresses the refrigerant gas. This process circulates to cool the liquid in the reservoir, the liquid with decreased temperature flows into the first body wrap through the third liquid inlet, providing the first body wrap with a cold compression function. Under the condition of the ambient temperature of 25-28° C., with an area of 1 $m^2$ of the first body wrap, a cooling rate is such that the surface temperature of the first body wrap reaches 5° C. within about 10 minutes, a cooling power is about 75 watts, and the achieved cooling capacity is about 250 watts. The system exhibits excellent cooling effects, high efficiency, stability, and low power consumption. In a second aspect, the first air pump and the first solenoid valve are provided to inflate the first body wrap, allowing the first body wrap to conform more closely to therapy areas. This enhances the therapy effect of the cold therapy with optional heat and compression therapy. Additionally, the combination of inflation and deflation allows the first body wrap to provide medical effects such as massage and compression. The system can be connected to the first body wrap, the second body wrap, the third body wrap for the use of three users at the same time, high utilization rate of equipment. The device has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir, which are able to directly or indirectly contact the liquid in the reservoir. This allows pre-cooling or pre-heating of the liquid, thereby enabling immediate use when the user requires therapy.

According to a third aspect, embodiments of the present disclosure provide a portable system for cold therapy with optional heat and compression therapy, applied to a first body wrap, including a cooling mechanism, a reservoir, and a control assembly; wherein the cooling mechanism comprises a compressor, a condenser, a fan, a heat exchanger, and the control assembly is electrically connected to the compressor, the condenser, the fan, respectively; and wherein: the compressor, the condenser, the fan, and the heat exchanger are placed outside the reservoir, respectively; the compressor has an air inlet connected to the heat exchanger through a first tube; the heat exchanger is connected to the condenser through a second tube; the condenser is connected to an air outlet of the compressor through a third tube; the first tube and the second tube are connected by fluid, and the second tube and the third tube are connected by fluid, enabling refrigerant in the compressor to pass through the condenser first and then through the heat exchanger to achieve a cooling effect; the fan has a working surface facing the condenser.

The reservoir comprises a first liquid outlet of the reservoir, wherein the liquid in the reservoir flows into the heat exchanger first through the first liquid outlet of the reservoir and then flows into the first body wrap; the liquid in the first body wrap can flow into the heat exchanger first and then flow into the first body wrap again, or the liquid in the first body wrap can flow back to the reservoir.

further comprising a heating mechanism, wherein the heating mechanism is electrically connected to the control assembly; the heating mechanism comprises a four-way valve, wherein the compressor is connected to the four-way valve and then to the heat exchanger through the first tube, and the condenser is connected to the four-way valve and then to the compressor through the third tube, and the four-way valve is controlled by the control assembly to change the flow direction, enabling refrigerant in the compressor to pass through the heat exchanger first and then through the condenser to achieve a heating effect; or the heating mechanism comprises one or more heating sheets, the one or more heating sheets are arranged on the outside of the heat exchanger.

In accordance with the portable system for cold therapy with optional heat and compression therapy provided in the present disclosure, the advantageous effects include the following. In a first aspect, the cooling mechanism is equipped with the compressor, the condenser, the fan, the heat exchanger. High temperature and high-pressure refrigerant gas is transported from the compressor to the condenser through the third tube, at this time, the temperature of the refrigerant gas is high, and the fan is utilized to cool the refrigerant gas in the condenser, and the refrigerant gas is liquefied. Refrigerant liquid is transported from the condenser to the heat exchanger through the second tube. In the heat exchanger, the refrigerant liquid undergoes heat exchange with the liquid in the heat exchanger, absorbs heat from the liquid and gasifies, and the liquid temperature decreases. Refrigerant gas is transported from the heat exchanger to the compressor through the first tube, and the compressor compresses the refrigerant gas. The heat exchanger is arranged on the outside of the reservoir, the liquid in the reservoir flows into the heat exchanger for cooling through the first liquid outlet of the reservoir and then flows into the first body wrap. The liquid in the first body wrap can flow into the heat exchanger for cooling again, or the liquid in the first body wrap can flow back into the reservoir, providing the first body wrap with a cold compression function, and the remaining liquid in the reservoir will no longer participate in the circulation, to greatly improve the cooling efficiency, and reduce the power consumption. Under the condition of the ambient temperature of 25-28° C., with an area of 1 m$^2$ of the first body wrap, a cooling rate is such that the surface temperature of the first body wrap reaches 5° C. within about 5 minutes, a cooling power is about 75 watts, and the achieved cooling capacity is about 250 watts. The system exhibits excellent cooling effects, high efficiency, stability, and low power consumption. In a second aspect, further comprising a heating mechanism, the heating mechanism comprises a four-way valve or one or more heating sheets, the control assembly controls the four-way valve to change the flow direction or control the heating sheet heating, to increase the temperature of the liquid in the heat exchanger, the liquid with increased temperature flows into the first body wrap through the third liquid inlet, providing the first body wrap with a hot compression function. Under the condition of the ambient temperature of 25-28° C., with an area of 1 m$^2$ of the first body wrap, a heating rate is such that the surface temperature of the first body wrap reaches 43° C. within about 6 minutes, a heating power is about 75-150 watts, and the achieved heating capacity is about 75-150 watts. The device exhibits excellent heating effects, high efficiency, and stability. The cooling and heating mechanisms are simultaneously incorporated into the portable device for cold therapy with optional heat and compression therapy, provided in the present disclosure. The device has a compact, small, and lightweight structure, facilitating convenient portability. The device is versatile, offering capabilities for cold compression, hot compression, and/or massage, enhancing the user experience.

According to a fourth aspect, embodiments of the present disclosure provide a portable device for cold therapy with optional heat and compression therapy, comprising a portable system for cold therapy with optional heat and compression therapy and a first body wrap; wherein the portable system for cold therapy with optional heat and compression therapy including a cooling mechanism, a reservoir, and a control assembly; wherein the cooling mechanism comprises a compressor, a condenser, a fan, a heat exchanger, and the control assembly is electrically connected to the compressor, the condenser, the fan, respectively; and wherein: the compressor, the condenser, the fan, and the heat exchanger are placed outside the reservoir, respectively; the compressor has an air inlet connected to the heat exchanger through a first tube; the heat exchanger is connected to the condenser through a second tube; the condenser is connected to an air outlet of the compressor through a third tube; the first tube and the second tube are connected by fluid, and the second tube and the third tube are connected by fluid, enabling refrigerant in the compressor to pass through the condenser first and then through the heat exchanger to achieve a cooling effect; the fan has a working surface facing the condenser.

The reservoir comprises a first liquid outlet of the reservoir, wherein the liquid in the reservoir flows into the heat exchanger first through the first liquid outlet of the reservoir and then flows into the first body wrap; the liquid in the first body wrap can flow into the heat exchanger first and then flow into the first body wrap again, or the liquid in the first body wrap can flow back to the reservoir.

further comprising a heating mechanism, wherein the heating mechanism is electrically connected to the control assembly; the heating mechanism comprises a four-way valve, wherein the compressor is connected to the four-way valve and then to the heat exchanger through the first tube, and the condenser is connected to the four-way valve and then to the compressor through the third tube, and the four-way valve is controlled by the control assembly to change the flow direction, enabling refrigerant in the compressor to pass through the heat exchanger first and then through the condenser to achieve a heating effect; or the heating mechanism comprises one or more heating sheets, the one or more heating sheets are arranged on the outside of the heat exchanger.

In accordance with the portable device for cold therapy with optional heat and compression therapy provided in the present disclosure, the advantageous effects include the following. In a first aspect, the cooling mechanism is equipped with the compressor, the condenser, the fan, the heat exchanger. High temperature and high-pressure refrigerant gas is transported from the compressor to the condenser through the third tube, at this time, the temperature of the refrigerant gas is high, and the fan is utilized to cool the refrigerant gas in the condenser, and the refrigerant gas is liquefied. Refrigerant liquid is transported from the condenser to the heat exchanger through the second tube. In the heat exchanger, the refrigerant liquid undergoes heat exchange with the liquid in the heat exchanger, absorbs heat from the liquid and gasifies, and the liquid temperature decreases. Refrigerant gas is transported from the heat exchanger to the compressor through the first tube, and the compressor compresses the refrigerant gas. The heat exchanger is arranged on the outside of the reservoir, the liquid in the reservoir flows into the heat exchanger for cooling through the first liquid outlet of the reservoir and then flows into the first body wrap. The liquid in the first body wrap can flow into the heat exchanger for cooling again, or the liquid in the first body wrap can flow back into the reservoir, providing the first body wrap with a cold compression function, and the remaining liquid in the reservoir will no longer participate in the circulation, to greatly improve the cooling efficiency, and reduce the power consumption. Under the condition of the ambient temperature of 25-28° C., with an area of 1 m$^2$ of the first body wrap, a cooling rate is such that the surface temperature of the first body wrap reaches 5° C. within about 5 minutes, a cooling power is about 75 watts, and the achieved cooling capacity is about 250 watts. The system exhibits excellent cooling effects, high efficiency, stability, and low power consumption. In a second aspect, further comprising a heating mechanism, the heating mechanism comprises a four-way valve or one or more heating sheets, the control assembly controls the four-way valve to change the flow direction or control the heating sheet heating, to increase the temperature of the liquid in the heat exchanger, the liquid with increased temperature flows into the first body wrap through the third liquid inlet, providing the first body wrap with a hot compression function. Under the condition of the ambient temperature of 25-28° C., with an area of 1 m$^2$ of the first body wrap, a heating rate is such that the surface temperature of the first body wrap reaches 43° C. within about 6 minutes, a heating power is about 75-150 watts, and the achieved heating capacity is about 75-150 watts. The device exhibits excellent heating effects, high efficiency, and stability. In a third aspect, the first air pump and the first solenoid valve are provided to inflate the first body wrap, allowing the first body wrap to conform more closely to therapy areas. This enhances the therapy effect of the cold therapy with optional heat and compression therapy. Additionally, the combination of inflation and deflation allows the first body wrap to provide medical effects such as massage and compression. The cooling and heating mechanisms are simultaneously incorporated into the portable device for cold therapy with optional heat and compression therapy, provided in the present disclosure. The device has a compact, small, and lightweight structure, facilitating convenient portability. The device is versatile, offering capabilities for cold compression, hot compression, and/or massage, enhancing the user experience.

In some examples, embodiments of the present disclosure provide a portable system for cold therapy with optional heat and compression therapy, applied to a first body wrap, including a body wrap cooling mechanism, a reservoir, and a control assembly; the body wrap cooling mechanism includes a compressor, a condenser, a fan, and a heat exchanger; the control assembly is electrically connected to the compressor, the condenser, and the fan, respectively; the compressor is placed outside the reservoir, and the condenser is placed adjacent to the reservoir and the fan, respectively; the heat exchanger is placed inside or underneath the reservoir, and is in direct or indirect contact with liquid in the reservoir to cool the liquid; the compressor has an air outlet connected to the heat exchanger through a first tube; the heat exchanger is connected to the condenser through a second tube; the condenser is connected to an air inlet of the compressor through a third tube; the first tube is communicated with the second tube, and the second tube is communicated with the third tube; the fan has a working surface facing the condenser; and the reservoir includes a liquid outlet of the reservoir and a liquid inlet of the reservoir, the liquid in the reservoir flows into the first body wrap through the liquid outlet of the reservoir, and liquid in the first body wrap flows into the reservoir through the liquid inlet of the reservoir.

The body wrap cooling mechanism is equipped with the compressor, the condenser, the fan, and the heat exchanger. Liquid gas is transported from the compressor to the heat exchanger through the first tube. In the heat exchanger, the liquid gas undergoes heat exchange with the liquid in the reservoir, absorbs heat from the liquid and gasifies, and the liquid temperature in the reservoir decreases. The gasified gas is then transported from the heat exchanger to the condenser through the second tube. At this point, the temperature of the gasified gas transported from the heat exchanger to the condenser is relatively high, and the fan is utilized to cool the gasified gas in the condenser. The cooled gas is then transported from the condenser to the compressor through the third tube, and the compressor compresses and liquefies the gas. This process circulates to cool the liquid in the reservoir. A cooling rate is such that the liquid in the reservoir decreases from room temperature to 5° C. within about 10 minutes. The cooling power is about 75 watts, and the achieved cooling capacity is about 150 watts. The system exhibits excellent cooling effects, high efficiency, stability, and low power consumption. The cooled liquid in the reservoir flows into the first body wrap through the liquid outlet of the reservoir. The liquid in the first body wrap flows into the reservoir through the liquid inlet of the reservoir, achieving a circulation of liquid and temperature reduction for cold therapy. The first body wrap is used for cold compression therapy on the body to achieve therapeutic effects. Additionally, an overall volume of the system is approximately 0.014 m$^3$, with a mass of about 3.8 kg, which has a compact, small, and lightweight structure, facilitating convenient portability.

In some embodiments, the heat exchanger includes a first cooling plate, and the first cooling plate is placed inside the reservoir; the first cooling plate is provided with a first air inlet and a first air outlet; and the first air inlet is connected to the first tube, and the first air outlet is connected to the second tube.

In some embodiments, the first cooling plate is further provided with an optional liquid inlet of the first cooling plate and an optional liquid outlet of the first cooling plate, and the optional liquid inlet of the first cooling plate is connected to the liquid inlet of the reservoir through a tube.

In some embodiments, the heat exchanger includes a spiral tube, and the spiral tube is placed inside the reservoir; and the spiral tube has one end connected to the first tube and the other end connected to the second tube.

In some embodiments, the heat exchanger includes a second cooling plate, and the second cooling plate is placed underneath the reservoir; the second cooling plate is provided with a second air inlet and a second air outlet, the second air inlet is connected to the first tube, and the second air outlet is connected to the second tube; and the reservoir includes a heat-conducting material.

In some embodiments, the reservoir is further provided with a liquid level detector and a temperature sensor inside, and the liquid level detector and the temperature sensor are both electrically connected to the control assembly.

In some embodiments, the second tube includes a capillary tube section, and the capillary tube section is placed between the heat exchanger and the condenser.

In some embodiments, the condenser includes a heat conduction tube, and the heat conduction tube is U-shaped and is bent along an inner wall of the condenser; and the heat conduction tube has one end extending out of the condenser to be connected to the capillary tube section and the other end extending out of the condenser to be connected to the compressor.

In some embodiments, the system further includes a water pump, the liquid outlet of the reservoir is connected to a liquid inlet of the first body wrap through the water pump, and the water pump is electrically connected to the control assembly; in response to the water pump working, the liquid in the reservoir flows into the first body wrap through the liquid outlet of the reservoir and the liquid inlet of the first body wrap, and the liquid in the first body wrap flows back into the reservoir through a liquid outlet of the body wrap and the liquid inlet of the reservoir.

In some embodiments, the system further includes a four-way valve, the compressor is connected to the four-way valve and then to the heat exchanger through the first tube, and the condenser is connected to the four-way valve and then to the compressor through the third tube; the four-way valve is electrically connected to the control assembly, and the four-way valve is controlled by the control assembly to change a gas flow direction, enabling air in the compressor to pass through the condenser first and then through the heat exchanger.

In some embodiments, the system further includes a body wrap heating mechanism, the body wrap heating mechanism includes a heating tube; and the heating tube is placed inside the reservoir and is electrically connected to the control assembly.

In some embodiments, the system further includes a first air pump, a first solenoid valve, and a first air tube; the first air pump is connected to the first air tube through the first solenoid valve, and the first air tube is connected to the first body wrap; the first air pump and the first solenoid valve are both electrically connected to the control assembly; and the first body wrap is inflated by the first air pump, and the first body wrap is deflated by the first solenoid valve.

In some embodiments, the system further includes a second air pump, a second solenoid valve, a third solenoid valve, a second air tube, and a third air tube; the second air pump is connected to the second air tube through the second solenoid valve, the second air pump is connected to the third air tube through the third solenoid valve, the second air tube is connected to a second body wrap, and the third air tube is connected to a third body wrap; the second air pump, the second solenoid valve, and the third solenoid valve are all electrically connected to the control assembly; and the second body wrap and the third body wrap are inflated by the second air pump, the second body wrap is deflated by the second solenoid valve, and the third body wrap is deflated by the third solenoid valve.

In some embodiments, the system further includes a housing, a bracket, and a connector, and the housing includes a bottom shell, an upper shell and a surface cover; the bracket is embedded in the housing, and the reservoir is placed on the bracket; an avoidance portion is provided on the bracket, and the condenser is embedded in the avoidance portion; an exterior side of the bottom shell is provided with a first groove, and the connector has one end inserted into the first groove and respectively connected to the liquid outlet of reservoir, the liquid inlet of the reservoir and the first air tube, and has the other end configured to be connected to a plurality of tubes, enabling the liquid outlet of the reservoir, the liquid inlet of the reservoir and the first air tube to be respectively connected to the first body wrap; the bottom shell is further provided with a first air hole and a second air hole, the first air hole and the second air hole are placed below the first groove; and one side of the first air hole is connected to the second air tube, one side of the second air hole is connected to the third air tube, and the other side of the first air hole and the other side of the second air hole are configured to be connected to tubes, enabling the second air tube to be connected to the second body wrap and the third air tube to be connected to the third body wrap.

In some embodiments, the control assembly further includes a circuit board, a display screen and a battery; the display screen is electrically connected to the circuit board; the display screen is placed on the surface cover; and an exterior side of the bottom shell is recessed towards the bracket to form a second groove, and the battery is placed in the second groove, and the battery includes a storage battery.

In some examples, embodiments of the present disclosure provide a portable device for cold therapy with optional heat and compression therapy, including the portable system for cold therapy with optional heat and compression therapy as described in any one of the embodiments. The portable device for cold therapy with optional heat and compression therapy includes a first body wrap, and the first body wrap is connected to the reservoir through the liquid outlet of the reservoir and the liquid inlet of the reservoir, respectively.

In accordance with the portable device for cold therapy with optional heat and compression therapy provided in the present disclosure, the advantageous effects include the following. In some examples, the body wrap cooling mechanism is equipped with the compressor, the condenser, the fan, and the heat exchanger. Liquid gas is transported from the compressor to the heat exchanger through the first tube. In the heat exchanger, the liquid gas undergoes heat exchange with the liquid in the reservoir, absorbs heat from the liquid and gasifies, and the liquid temperature decreases. The gasified gas is then transported from the heat exchanger to the condenser through the second tube. At this point, the temperature of the gasified gas transported from the heat exchanger to the condenser is relatively high, and the fan is utilized to cool the gasified gas in the condenser. The cooled gas is then transported from the condenser to the compressor through the third tube, and the compressor compresses and liquefies the gas. This process circulates to cool the liquid in the reservoir. A cooling rate is such that the liquid decreases from room temperature to 5° C. within about 10 minutes. A cooling power is about 75 watts, and the achieved cooling capacity is about 150 watts. The system exhibits excellent cooling effects, high efficiency, stability, and low power consumption. The liquid with decreased temperature flows into the body wrap through the liquid inlet of the body wrap, providing the body wrap with a cold compression function. In some examples, the air pumps and the solenoid valves are provided to inflate the body wrap, allowing the body wrap to conform more closely to therapy areas. This enhances the therapy effect of the cold therapy with optional heat and compression therapy. Additionally, the combination of inflation and deflation allows the body wrap to provide medical effects such as massage and compression. In some examples, the compressor, condenser, and fan are paused by the control assembly. The heating tube is activated by the control assembly to increase the temperature of the liquid in the reservoir. A heating rate is such that the liquid reaches 43° C. from room temperature within about 6 minutes. The heating power is about 150 watts, and the achieved heating capacity is about 150 watts. The device exhibits excellent heating effects, high efficiency, and stability. The liquid with increased temperature flows into the body wrap through the liquid inlet of the body wrap, providing the body wrap with a hot compression function. The cooling and heating mechanisms are simultaneously incorporated into the portable device for cold therapy with optional heat and compression therapy, provided in the present disclosure. The overall volume of the device is approximately 0.014 m$^3$, with a mass of about 3.8 kg, which has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir, which are able to directly or indirectly contact the liquid in the reservoir. This allows pre-cooling or pre-heating of the liquid, thereby enabling immediate use when the user requires therapy.

BRIEF DESCRIPTION OF THE DRAWINGS

In order to more clearly illustrate the embodiments of the present disclosure or conventional technical solutions, accompanying drawings required in the embodiments or conventional technical solutions are briefly described below. It is apparent that the accompany drawings in the following description are merely some embodiments of the present disclosure. For a person of ordinary skills in the art, other drawings may also be obtained according to these drawings.

DETAILED DESCRIPTION

Figure 1:
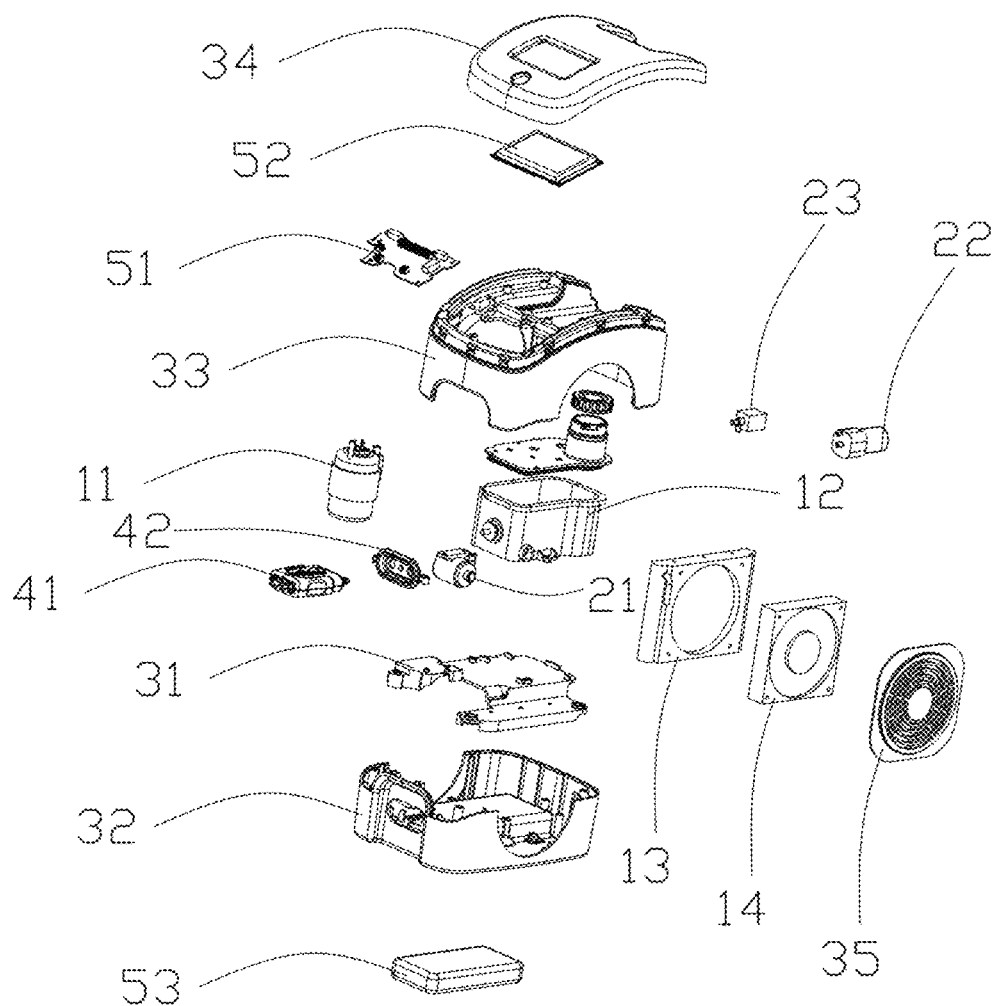
FIG. 1 is an exploded schematic structural diagram of a portable system for cold therapy with optional heat and compression therapy according to an embodiment of the present disclosure.

In order to enable the skilled person in the art to better understand technical solutions in the present disclosure, the technical solutions in the embodiments of the present disclosure will be described clearly and completely in combination with the accompanying drawings in the embodiments of the present disclosure. It is apparent that the described embodiments are only some of the embodiments, but not all the embodiments of the present disclosure. Based on the embodiments in the present disclosure, all other embodiments obtained by persons having ordinary skills in the art without creative works are within the protection scope of the present disclosure.

It should be noted that when a component is referred to as "fixed" or "placed on" another component, it is able to be directly or indirectly on the other component. When a component is referred to as "connected" to another component, it is able to be directly or indirectly connected to the other component.

In addition, the terms "first" and "second" are used for descriptive purposes only and are not to be understood as indicating or implying relative importance or as implicitly indicating the quantity of technical features indicated. Thus, a feature defined as "first" or "second" may explicitly or implicitly include one or more such features. In the description of the present disclosure, "plurality of" or "several" means two or more unless otherwise expressly specified.

It should be noted that structures, proportions, sizes, etc., depicted in the accompanying drawings are provided only to facilitate the comprehension and reading of the disclosed contents for those skilled in the art. They are not intended to limit the conditions under which the present disclosure able to be implemented and do not hold technical significance. Any modifications to the structures, changes in proportions, or adjustments in size that do not affect the effectiveness and objectives achievable by the present disclosure should still fall within the scope of the technical contents disclosed in the present disclosure. The numbering of the components in the figures is listed as below.

11: Compressor; 12: Reservoir; 121: First liquid inlet of the reservoir; 122: First liquid outlet of the reservoir; 123: Second adapter; 13: Condenser; 14: Fan; 15: Heat exchanger; 151: First cooling plate; 1511: First air outlet of the first cooling plate; 1512: First air inlet of the first cooling plate; 1513: Second liquid inlet of the first cooling plate; 1514: second liquid outlet of the first cooling plate; 152: Spiral tube; 153: Second cooling plate; 1531: Second air outlet of the second cooling plate; 1532: Second air inlet of the second cooling plate; 154: Third cooling plate; 1541: Third air inlet of the third cooling plate; 1542: Third air outlet of the third cooling plate; 1543: Fourth liquid inlet of the third cooling plate; 1544: Fourth liquid outlet of the third cooling plate; 16: Heating tube; 161: Heating sheet; 171: First tube; 172: Second tube; 173: Third tube; 174: First air tube; 175: Second air tube; 176: Third air tube; 177: Fourth tube; 178: Fifth tube; 179: Sixth tube; 180: Seventh tube; 181: Eighth tube; 18: Four-way valve; 19: Three-way connector; 191: First connector; 192: Second connector; 193: Third connector; 21: Water pump; 22: First air pump; 23: First solenoid valve; 24: Second air pump; 25: Second solenoid valve; 26: Third solenoid valve; 27: Pressure relief valve; 31: Bracket; 32: Bottom shell; 321: First groove; 322: Second groove; 33: Upper shell; 34: Surface cover; 35: Dust cover; 41: Connector; 42: Connector base; 51: Main control board; 52: Display screen; 53: Battery; 61: Liquid level detector; 62: Temperature sensor; 63: Pressure sensor; 71: First air hole; 72: Second air hole; A: First body wrap; A1: Third liquid inlet; A2: Third liquid outlet; B: Second body wrap; C: Third body wrap; M: Portable device for cold therapy with optional heat and compression therapy.

In some examples, referring to FIG. 1 to FIG. 15 and FIG. 28 to FIG. 29, the present disclosure provides a portable system for cold therapy with optional heat and compression therapy, applied to a first body wrap A, including a cooling mechanism, a reservoir 12, and a control assembly. The cooling mechanism includes a compressor 11, a condenser 13, a fan 14, and a heat exchanger 15. The control assembly is electrically connected to the compressor 11, the condenser 13, and the fan 14, respectively. The compressor 11 is placed outside the reservoir 12, and the condenser 13 is respectively placed adjacent to the reservoir 12 and the fan 14. The heat exchanger 15 is placed inside and/or underneath the reservoir 12 and is in direct and/or indirect contact with liquid in the reservoir 12 to cool the liquid. An air inlet of the compressor 11 is connected to the heat exchanger 15 through a first tube 171. The heat exchanger 15 is connected to the condenser 13 through a second tube 172. The condenser 13 is connected to an air outlet of the compressor 11 through a third tube 173. The first tube 171 is communicated with the second tube 172 (e.g., connected by fluid), and the second tube 172 is communicated with the third tube 173 (e.g., connected by fluid). This enables refrigerant gas in the compressor 11 to pass through the condenser 13 and then through the heat exchanger 15 to achieve a cooling effect; the fan 14 has a working surface facing the condenser 13. The heat exchanger 15 comprises a first cooling plate 151 placed inside the reservoir 12; wherein the first cooling plate 151 comprises a first air inlet of the first cooling plate 1512, a first air outlet of the first cooling plate 1511, a second liquid inlet of the first cooling plate 1513, and a second liquid outlet of the first cooling plate 1514; and wherein the first air outlet of the first cooling plate 1511 is connected to the first tube 171, and the first air inlet of the first cooling plate 1512 is connected to the second tube 172; and the second liquid inlet of the first cooling plate 1513 is connected to the first liquid inlet of the reservoir 121 through a fourth tube 177. In some examples, a working surface of the fan 14 faces the condenser 13. The reservoir 12 includes a first liquid outlet of the reservoir 122 and a first liquid inlet of the reservoir 121. The liquid in the reservoir 12 flows into the first body wrap A through the liquid outlet of the reservoir 122, and liquid in the first body wrap A flows into the reservoir 12 through the first liquid inlet of the reservoir 121.

It should be noted that the compressor 11, the condenser 13, the fan 14 and the heat exchanger 15 can all be one or more. A plurality of the compressors 11 are arranged in series. A plurality of the condenser 13 are arranged in series, each working face of the fan 14 is toward the condenser 13. A plurality of the heat exchangers 15 are arranged in series.

It should be noted that the liquid includes water, alcohol, antifreezing solution, and the like. Preferably, a concentration of the alcohol is 10%.

Figure 2:
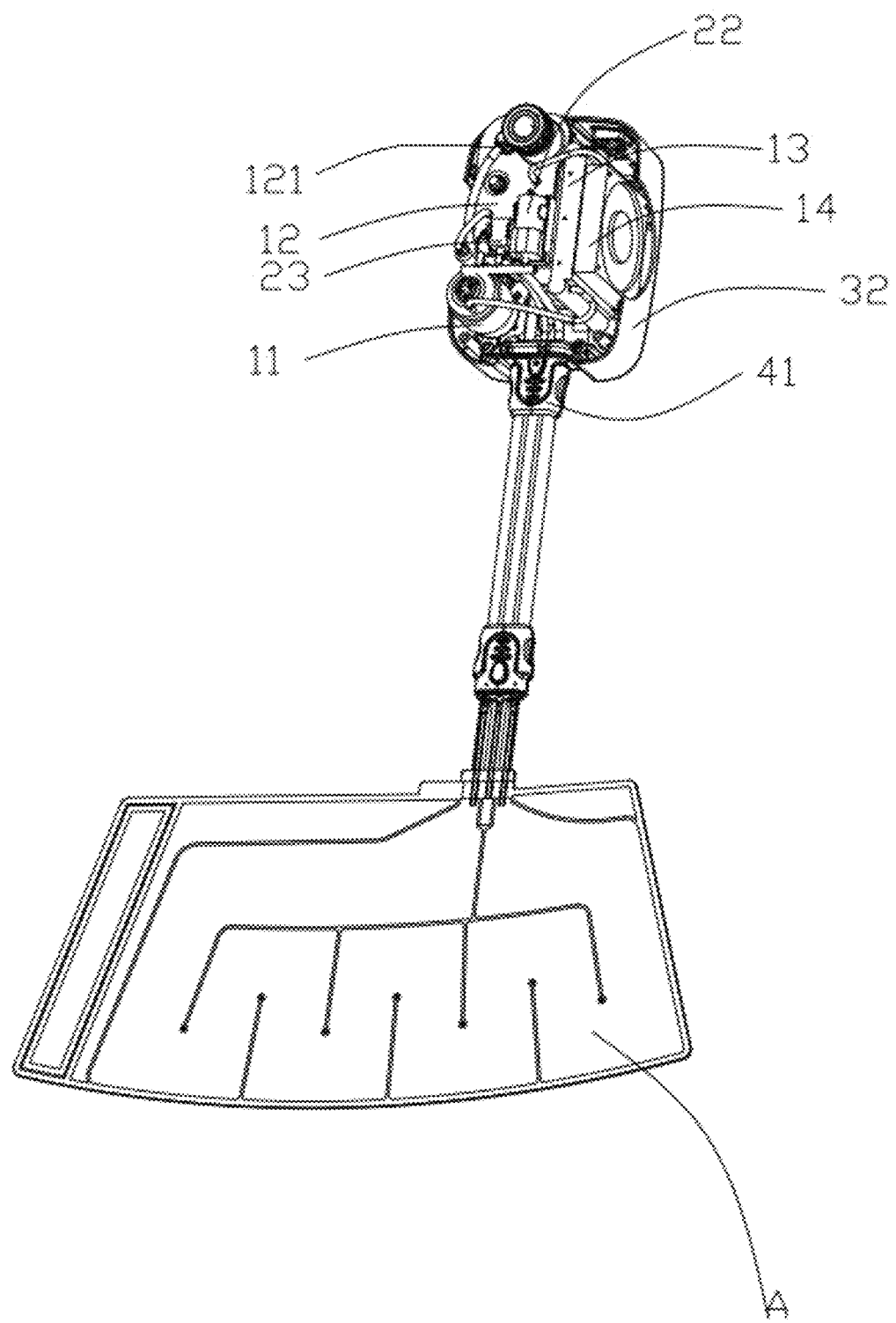
FIG. 2 is a first partial schematic structural diagram of a portable device for cold therapy with optional heat and compression therapy according to an embodiment of the present disclosure.
Figure 3:
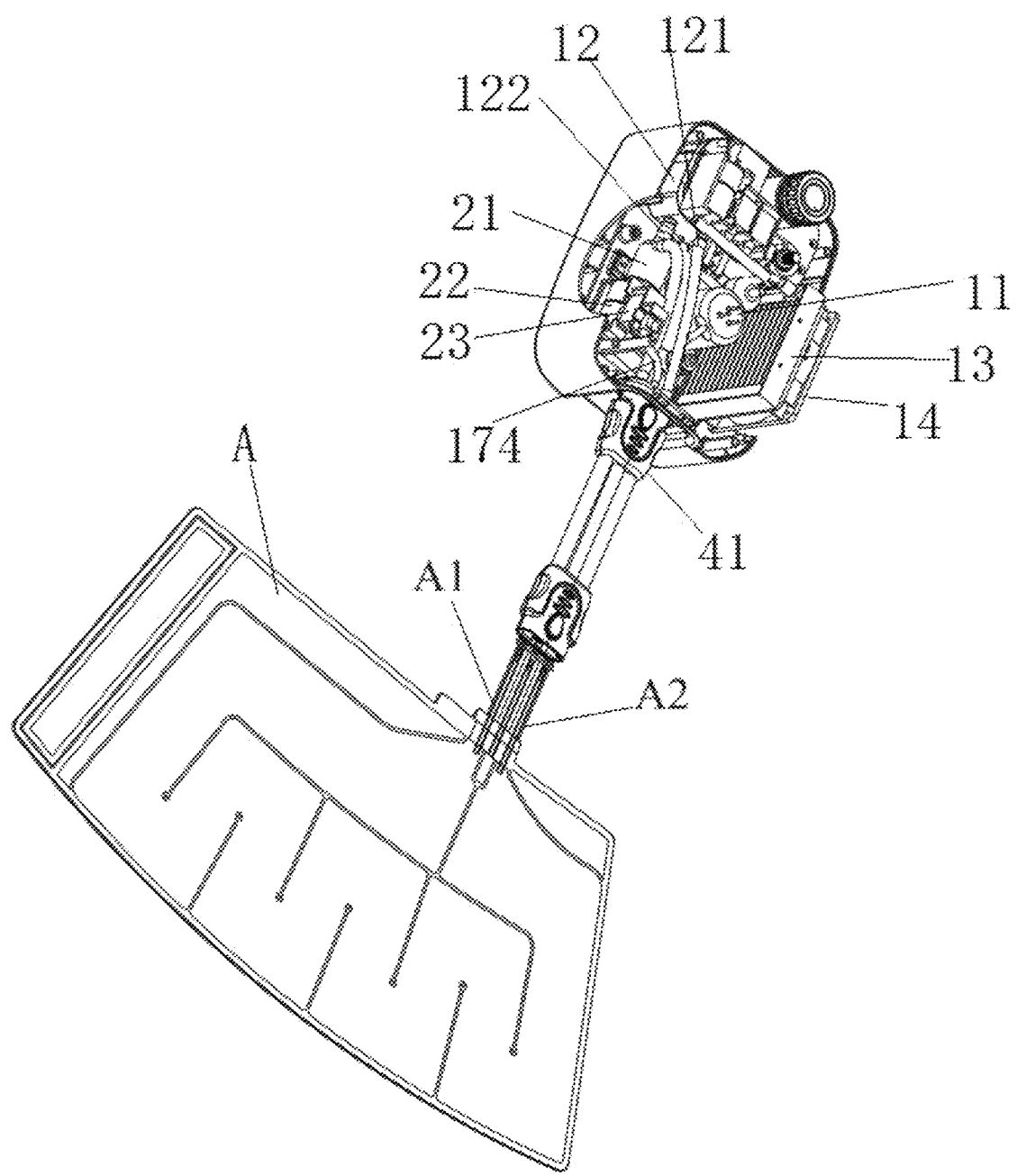
FIG. 3 is a second schematic structural diagram of a portable device for cold therapy with optional heat and compression therapy according to an embodiment of the present disclosure.
Figure 6:
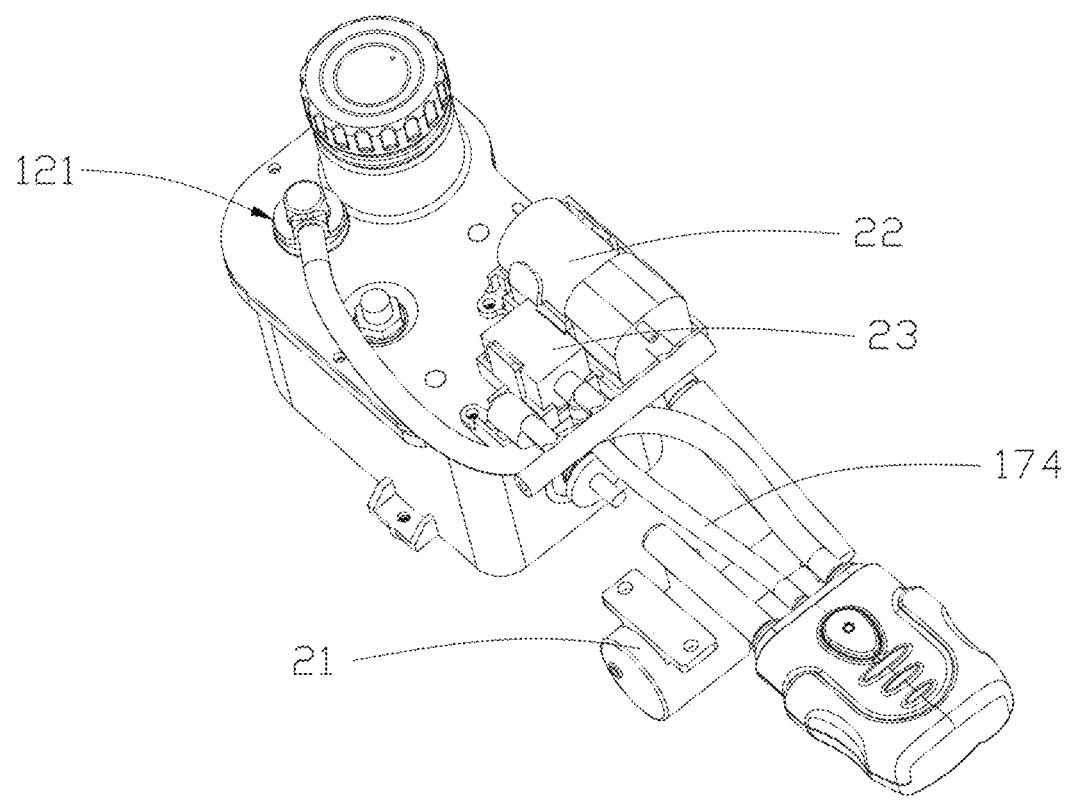
FIG. 6 is a second schematic structural diagram of a portable system for cold therapy with optional heat and compression therapy according to an embodiment of the present disclosure.
Figure 12:
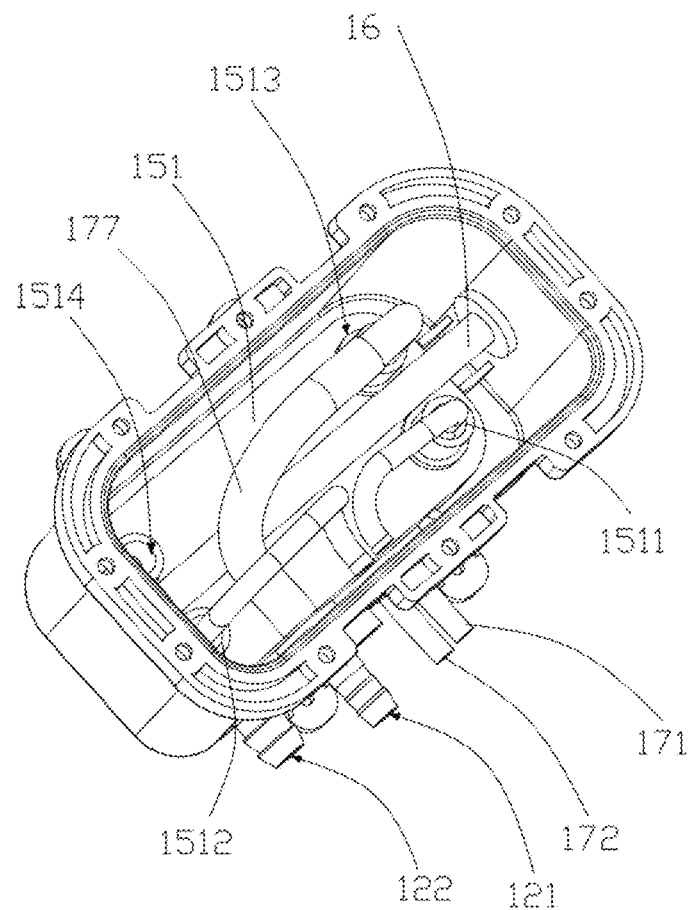
FIG. 12 is a second partial schematic structural diagram of a portable system for cold therapy with optional heat and compression therapy in the manner of the heat exchanger being the first cooling plate.

It should be noted that the first liquid inlet of the reservoir 121 may be placed at the top of the reservoir 12 as shown in FIG. 2 and FIG. 6, and the first liquid inlet of the reservoir 121 may also be placed on the side of the reservoir 12 as shown in FIG. 3 and FIG. 12.

It should be noted that a branch of the first tube 171 is provided with a cooling agent adding port, so as to maintain temperature of the cooling when the body wrap cooling mechanism works for a long time. When using the body wrap cooling mechanism in long-term circles, it may not achieve the heat exchange in an ideal state and the cooling effect cannot reach the expectation, thus the cooling agent is periodically added to improve the cooling effect.

It should be noted that the first cooling plate 151 includes a brazed plate heat exchanger. The liquid in the first body wrap A flows into the second liquid inlet of the first cooling plate 1513 through the first liquid inlet of the reservoir 121, and the liquid flows into the reservoir 12 through the second liquid outlet of the first cooling plate 1514 after being cooled in the brazed plate heat exchanger.

It should be noted that the first tube 171 is communicated with the second tube 172 (e.g., connected by fluid), and the second tube 172 is communicated with the third tube 173 (e.g., connected by fluid). In fact, the first tube 171, the second tube 172 and the third tube 173 are all part of the same tube, and the same tube is connected to the compressor 11, the heat exchanger 15 and the condenser 13 to form a closed circulation loop. For example, the first tube 171 includes a compressor section, a first tube connecting section extending out of the compressor 11 to connect the heat exchanger 15, and a heat exchanger section. The second tube 172 includes a second tube connecting section extending out of the heat exchanger 15 to connect the condenser 13, and a condenser section. The third tube 173 includes a third tube connecting section extending out of the condenser 13 to connect the compressor 11.

It should be noted that the refrigerant flows into the first cooling plate 151 through the second tube 172, the first air inlet of the first cooling plate 1512, and then returns to the compressor 11 through the first air outlet of the first cooling plate of 1511 and the first tube 171 to cool the first cooling plate 151 and exchange heat with the liquid in the first cooling plate 151, so that the temperature of the liquid decreases.

The technical problems to be solved in the embodiments lie in insufficient cooling effect and low efficiency of the body wrap cooling mechanism.

Figure 28:
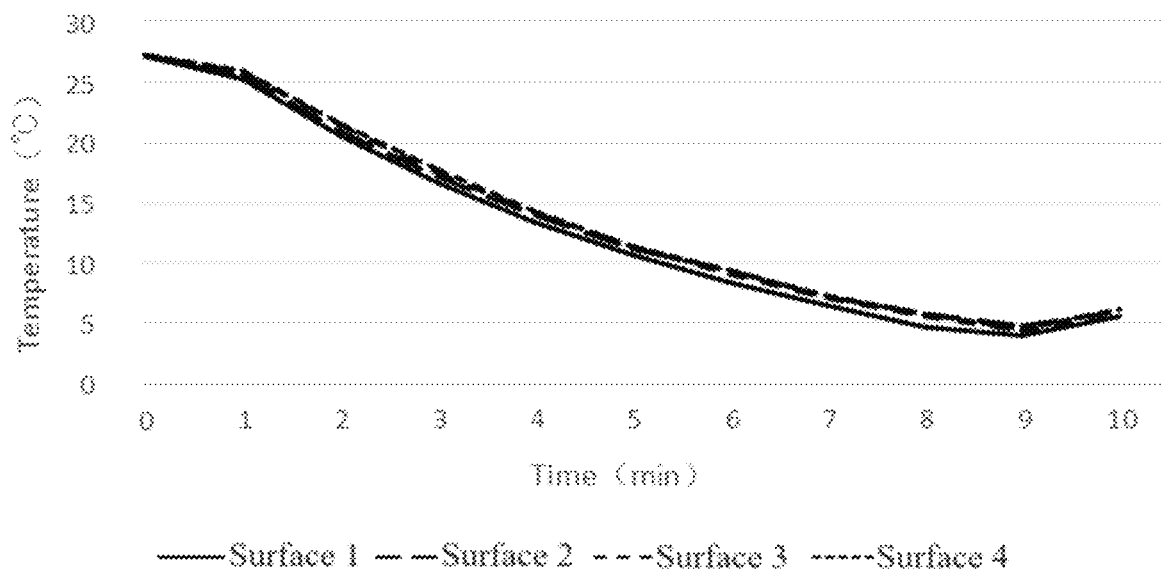
FIG. 28 is a cooling temperature profile on multiple surface locations of the first body wrap according to an embodiment of the present disclosure.
Figure 29:
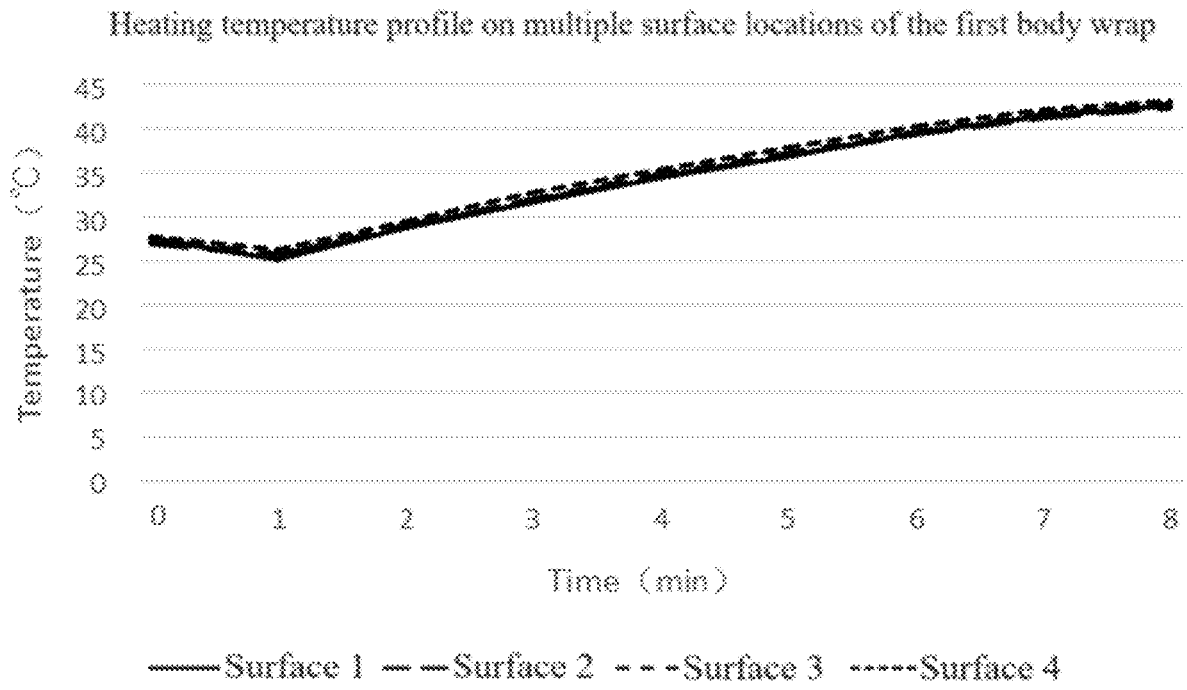
FIG. 29 is a heating temperature profile on multiple surface locations of the first body wrap according to an embodiment of the present disclosure.

The portable system for cold therapy with optional heat and compression therapy according to the present disclosure has the following beneficial effects. That is, the body wrap cooling mechanism is provided with the compressor 11, the condenser 13, the fan 14 and the heat exchanger 15. In some examples, the liquid gas is transported from the compressor 11 to the heat exchanger 15 through the first tube 171. In the heat exchanger 15, the liquid gas undergoes heat exchange with the liquid in the reservoir 12, absorbs heat from the liquid and gasifies, and the liquid temperature decreases. The gasified gas is then transported from the heat exchanger 15 to the condenser 13 through the second tube 172. At this point, the temperature of the gasified gas transported from the heat exchanger 15 to the condenser 13 is relatively high, and the fan 14 is used to cool the gasified gas in the condenser 13. The cooled gas is then transported from the condenser 13 to the compressor 11 through the third tube 173, and the compressor 11 compresses and liquefies the gas. In some examples, high temperature and high-pressure refrigerant gas is transported from the compressor 11 to the condenser 13 through the third tube 173, at this time, the temperature of the refrigerant gas is high, and the fan 14 is utilized to cool the refrigerant gas in the condenser 13, and the refrigerant gas is liquefied. Refrigerant liquid is transported from the condenser 13 to the heat exchanger 15 through the second tube 172. In the heat exchanger 15, the refrigerant liquid undergoes heat exchange with the liquid in the reservoir 12, absorbs heat from the liquid and gasifies, and the liquid temperature decreases. Refrigerant gas is transported from the heat exchanger 15 to the compressor 11 through the first tube 171, and the compressor 11 compresses the refrigerant gas. This process circulates to cool the liquid in the reservoir 12, the liquid with decreased temperature flows into the first body wrap A through the third liquid inlet A1, providing the first body wrap A with a cold compression function. Referring to FIG. 28, under the condition of the ambient temperature of 25-28° C., with an area of 1 m² of the first body wrap A. A cooling rate is such that the liquid decreases from room temperature to 5° C. within about 10 minutes. A cooling power is about 75 watts, and the achieved cooling capacity is about 150 to 250 watts. The system exhibits excellent cooling effects, high efficiency, stability, and low power. The liquid with decreased temperature in the reservoir 12 flows into the first body wrap A through the first liquid outlet of the reservoir 122, and the liquid in the first body wrap A flows into the reservoir through the first liquid inlet of the reservoir 121, achieving a circulation of liquid and temperature reduction. The first body wrap A is used for cold compression therapy on the body to achieve therapeutic effects. Additionally, in some examples, an overall volume of the system is approximately 0.014 m³, with a mass of about 3.8 kg, which has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir 12, which are able to directly or indirectly contact the liquid in the reservoir 12. This allows pre-cooling or pre-heating of the liquid, thereby enabling immediate use when the user requires therapy.

In some embodiments, the reservoir is further provided with a liquid level detector and a temperature sensor inside, and the liquid level detector and the temperature sensor are both electrically connected to the control assembly.

In some embodiments, the second tube comprises a throttle device, and the throttle device is placed between the heat exchanger and the condenser; and wherein the condenser comprises a heat conduction tube, and the heat conduction tube has one end extending out of the condenser to be connected to the throttle device and another end extending out of the condenser to be connected to the compressor.

In some embodiments, further comprising a water pump, wherein the first liquid outlet of the reservoir is connected to a third liquid inlet of the first body wrap through the water pump, and the water pump is electrically connected to the control assembly; and wherein, in response to the water pump working, the liquid in the reservoir flows into the first body wrap through the first liquid outlet of the reservoir and the third liquid inlet, and the liquid in the first body wrap flows back into the reservoir through a third liquid outlet of the first body wrap and the first liquid inlet of the reservoir.

In some embodiments, further comprising a four-way valve, wherein the compressor is connected to the four-way valve and then to the heat exchanger through the first tube, and the condenser is connected to the four-way valve and then to the compressor through the third tube; and wherein, the four-way valve is electrically connected to the control assembly, and the four-way valve is controlled by the control assembly to change the flow direction, enabling refrigerant gas in the compressor to pass through the heat exchanger first and then through the condenser to achieve a heating effect.

In some embodiments, further comprising a heating mechanism, wherein the heating mechanism comprises a heating tube; and wherein the heating tube is placed inside the reservoir and is electrically connected to the control assembly.

In some embodiments, further comprising a first air pump, a first solenoid valve, and a first air tube; wherein: the first air pump is connected to the first body wrap through the first air tube, and the first solenoid valve is arranged on the first air tube; the first air pump and the first solenoid valve are both electrically connected to the control assembly; and the first body wrap is configured to be inflated by the first air pump, and the first body wrap is configured to be deflated by the first solenoid valve.

In some embodiments, further comprising a second air pump, a second solenoid valve, a third solenoid valve, a second air tube, and a third air tube; wherein: the second air pump is connected to the second body wrap through the second air tube, and the second solenoid valve is arranged on the second air tube; the second air pump is connected to the third body wrap through the third air tube, and the third solenoid valve is arranged on the third air tube; the second air pump, the second solenoid valve, and the third solenoid valve are all electrically connected to the control assembly; and the second body wrap and the third body wrap are configured to be inflated by the second air pump, the second body wrap is configured to be deflated by the second solenoid valve, and the third body wrap is configured to be deflated by the third solenoid valve.

In some embodiments, further comprising a housing, a bracket, and a connector, wherein the housing comprises a bottom shell, an upper shell and a surface cover; and wherein: the bracket is embedded in the housing, and the reservoir is placed on the bracket; an avoidance portion is displayed on the bracket, wherein the condenser is embedded in the avoidance portion; an exterior side of the bottom shell is provided with a first groove, wherein the connector has one end inserted into the first groove and respectively connected to the first liquid outlet of the reservoir, the first liquid inlet of the reservoir and the first air tube, and has another end configured to be connected to a plurality of tubes, enabling the first liquid outlet of the reservoir, the first liquid inlet of the reservoir and the first air tube to be respectively connected to the first body wrap; and the bottom shell is further provided with a first air hole and a second air hole, wherein the first air hole and the second air hole are placed below the first groove; and wherein one side of the first air hole is connected to the second air tube, one side of the second air hole is connected to the third air tube, and another side of the first air hole and another side of the second air hole are configured to be connected to tubes, enabling the second air tube to be connected to the second body wrap and the third air tube to be connected to the third body wrap.

In some embodiments, the control assembly further comprises a main control board, a display screen, and a battery; and wherein: the display screen and the battery are both electrically connected to the main control board; the display screen is placed on the surface cover; and an exterior side of the bottom shell is recessed towards the bracket to form a second groove, wherein the battery is placed in the second groove, and the battery comprises a storage battery.

In one embodiment, a liquid level detector 61 and a temperature sensor 62 are further provided in the reservoir 12, and the liquid level detector 61 and the temperature sensor 62 are both electrically connected to the control assembly.

It should be noted that the liquid level detector 61 is placed in the reservoir 12 for detecting a height of a liquid position. The temperature sensor 62 is placed on the side of the reservoir 12 for detecting temperature of the liquid in the reservoir 12, to control the temperature by means of the control assembly to achieve a suitable cold compression or hot compression effect.

In one embodiment, the second tube 172 comprises a throttle device, and the throttle device is placed between the heat exchanger 15 and the condenser 13; the condenser 13 comprises a heat conduction tube; and wherein the heat conduction tube has one end extending out of the condenser 13 to be connected to the throttle device and another end extending out of the condenser 13 to be connected to the compressor 11.

It should be noted that the second tube 172 includes a second tube connecting section extending out of the heat exchanger 15 to connect the condenser 13, and a condenser section. The throttle device is placed on the second tube connecting section extending out of the heat exchanger 15 to connect the condenser 13. The throttle device may be a capillary tube section, the second tube connecting section extends out of the heat exchanger 15 with a tendency of reduced tube diameter to form the capillary tube section. Preferably, the diameter is reduced to 3-6 times the diameter of the original tube (i.e., the second tube connecting section). The throttle device may also be a throttle valve or other throttle step-down device.

It should be noted that, after the refrigerant liquid passes through the capillary tube section with a small diameter, a flowing speed of the refrigerant liquid becomes slow due to a small sectional area of the capillary tube section, so that pressure of the refrigerant liquid is reduced, and meanwhile, the temperature of the refrigerant liquid is reduced. At this point, high-temperature and high-pressure refrigerant liquid just output from the condenser 13 is able to be depressurized through the capillary tube section.

It should be noted that the heat conduction tube includes a copper tube. High temperature and high-pressure refrigerant gas enters the condenser section, and the condenser section is provided with a copper tube. Heat of the refrigerant gas is absorbed and gradually dissipated into surrounding environment by using the copper tube. Meanwhile, the working surface of the fan 14 faces a position of the copper tube in the condenser 13, further makes the refrigerant cooling liquid. The refrigerant liquid subjected to heat dissipation through the copper tube and the fan 14 is conveyed back to the compressor 11 through the third tube 173.

In one embodiment, a water pump 21 is further provided, the first liquid outlet of the reservoir 122 is connected to a third liquid inlet A1 of the first body wrap A through the water pump 21, and the water pump 21 is electrically connected to the control assembly. In response to the water pump 21 working, the liquid in the reservoir 12 flows into the first body wrap A through the first liquid outlet of the reservoir 122 and the third liquid inlet A1, and the liquid in the first body wrap A flows back into the reservoir 12 through a third liquid outlet A2 of the first body wrap and the first liquid inlet of the reservoir 121.

Figure 11:
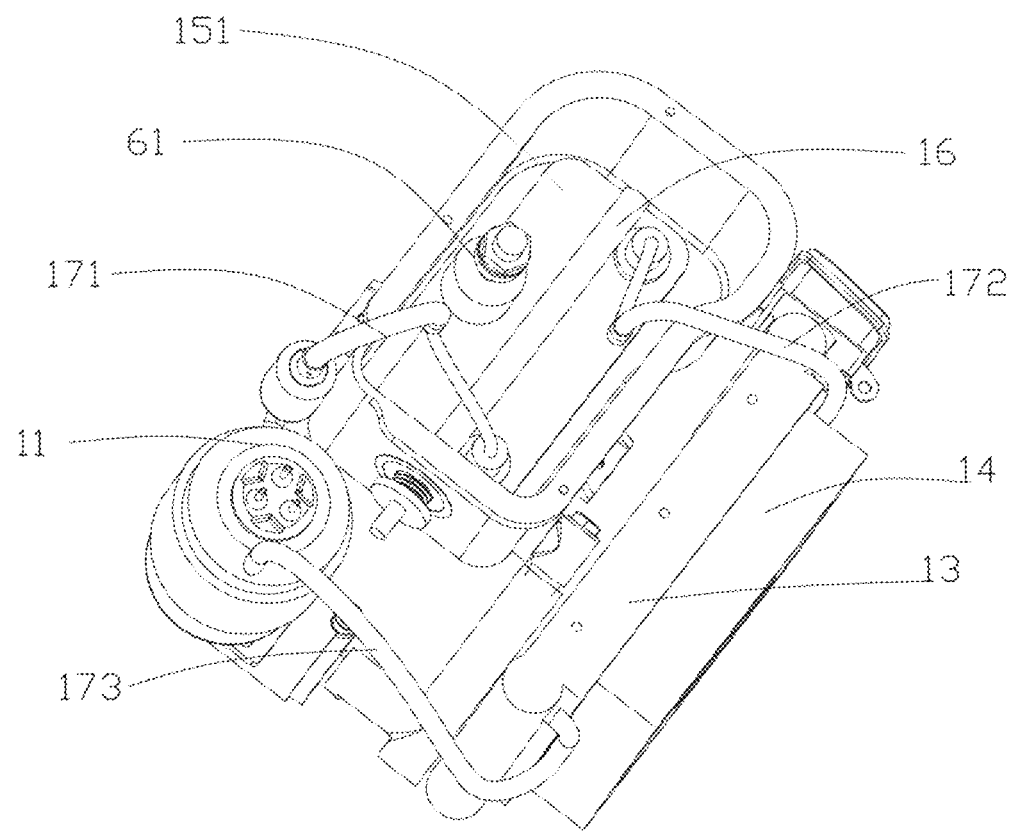
FIG. 11 is a first partial schematic structural diagram of a portable system for cold therapy with optional heat and compression therapy in a manner of a heat exchanger being a first cooling plate.

In one embodiment, referring to FIG. 11, the heat exchanger 15 includes a first cooling plate 151, and the first cooling plate 151 is placed inside the reservoir 12. The first cooling plate 151 is provided with a first air inlet 1511 and a first air outlet 1512. The first air inlet 1511 is connected to the first tube 171, and the first air outlet 1512 is connected to the second tube 172.

It should be noted that the liquid gas enters the first cooling plate 151 in the reservoir 12 through the first tube 171 and the first air inlet 1511 and then exits through the first air outlet 1512 and the second tube 172. This process allows the first cooling plate 151 to cool down and undergo heat exchange with the liquid in the reservoir 12, thereby reducing temperature of the liquid in the reservoir 12.

Figure 13:
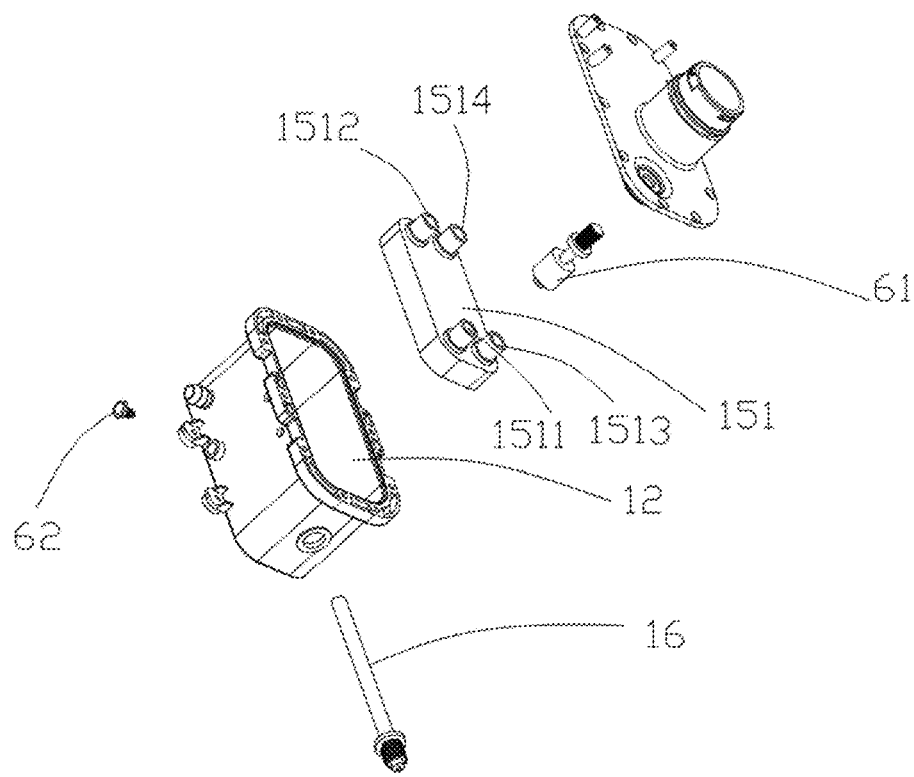
FIG. 13 is a partial exploded schematic structural structure of a portable system for cold therapy with optional heat and compression therapy in the manner of the heat exchanger being the first cooling plate.

In one embodiment, referring to FIG. 12 and FIG. 13, the first cooling plate 151 is further provided with a liquid inlet 1513 of the first cooling plate and a liquid outlet 1514 of the first cooling plate, and the liquid inlet 1513 of the first cooling plate is connected to the first liquid inlet of the reservoir 121 through a tube.

It should be noted that the first cooling plate 151 includes a brazed plate heat exchanger. The liquid in the first body wrap A flows into the liquid inlet 1513 of the first cooling plate through the first liquid inlet of the reservoir 121, and the liquid flows into the reservoir 12 through the liquid outlet 1514 of the first cooling plate after being cooled in the brazed plate heat exchanger.

Figure 14:
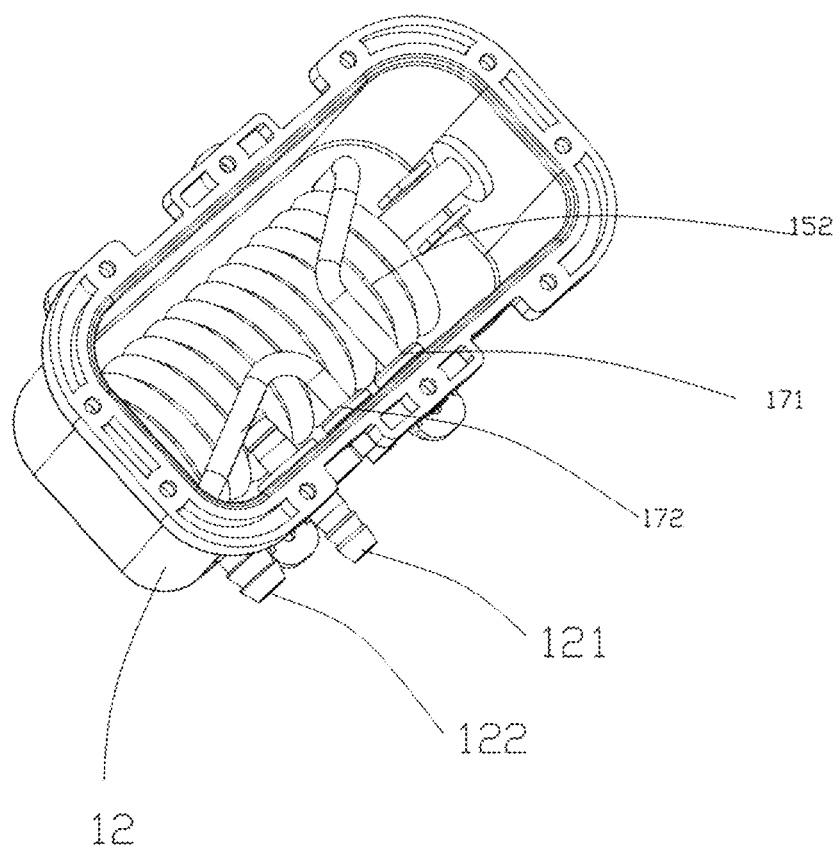
FIG. 14 is a partial schematic structural diagram of a portable system for cold therapy with optional heat and compression therapy in a manner of the heat exchanger being a spiral copper tube.

In one embodiment, referring to FIG. 14, the heat exchanger 15 includes a spiral tube 152, and the spiral tube 152 is placed inside the reservoir 12. One end of the spiral tube 152 is connected to the first tube 171, and the other end of the spiral tube 152 is connected to the second tube 172.

It should be noted that the spiral tube 152 includes a copper material or a stainless-steel material. Gas enters the spiral tube 152 in the reservoir 12 through the first tube 171 and then exits through the second tube 172, so that the spiral tube 152 is cooled, and then the temperature of the liquid in the reservoir 12 is reduced through the spiral tube 152. The spiral structure of the spiral tube 152 enables cold gas conveyed by the compressor 11 to stay in the spiral tube 152 for a longer time and increases a contact area between the spiral tube 152 with the liquid in the reservoir 12, so as to perform sufficient heat exchange with the liquid, thereby improving the cooling efficiency during cold therapy.

Figure 15:
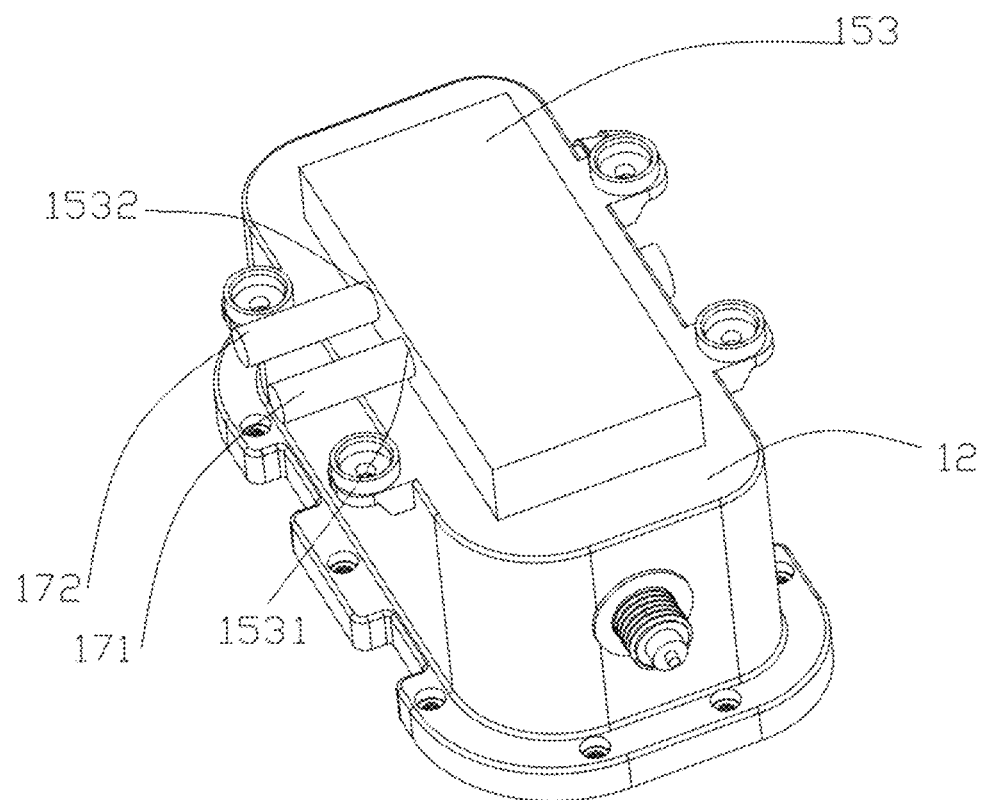
FIG. 15 is a partial schematic structural diagram of a portable system for cold therapy with optional heat and compression therapy in a manner of the heat exchanger being a second cooling plate manner.
Figure 16:
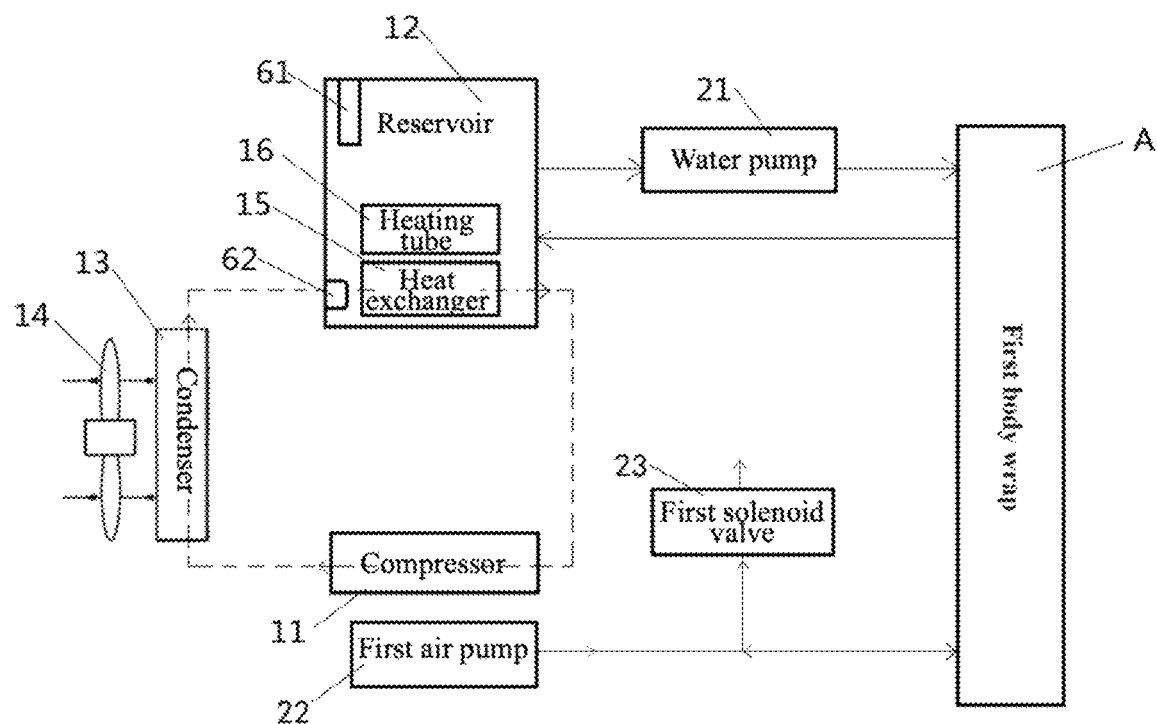
FIG. 16 is a first structural block diagram of a portable device for cold therapy with optional heat and compression therapy according to an embodiment of the present disclosure.
Figure 17:
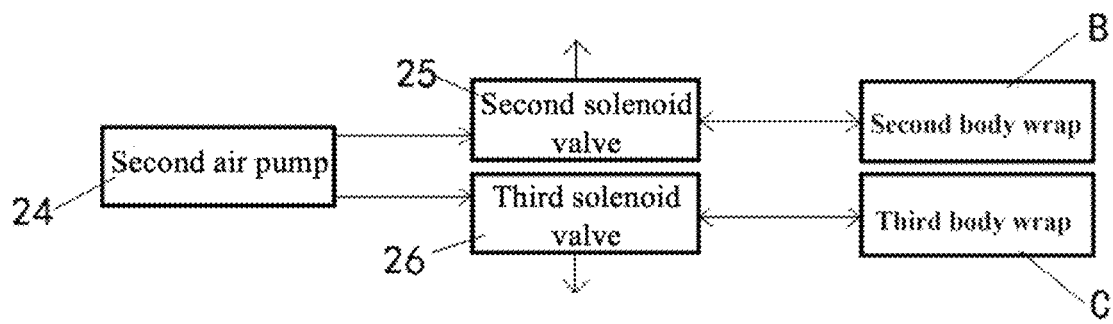
FIG. 17 is a second structural block diagram of a portable device for cold therapy with optional heat and compression therapy according to an embodiment of the present disclosure.
Figure 18:
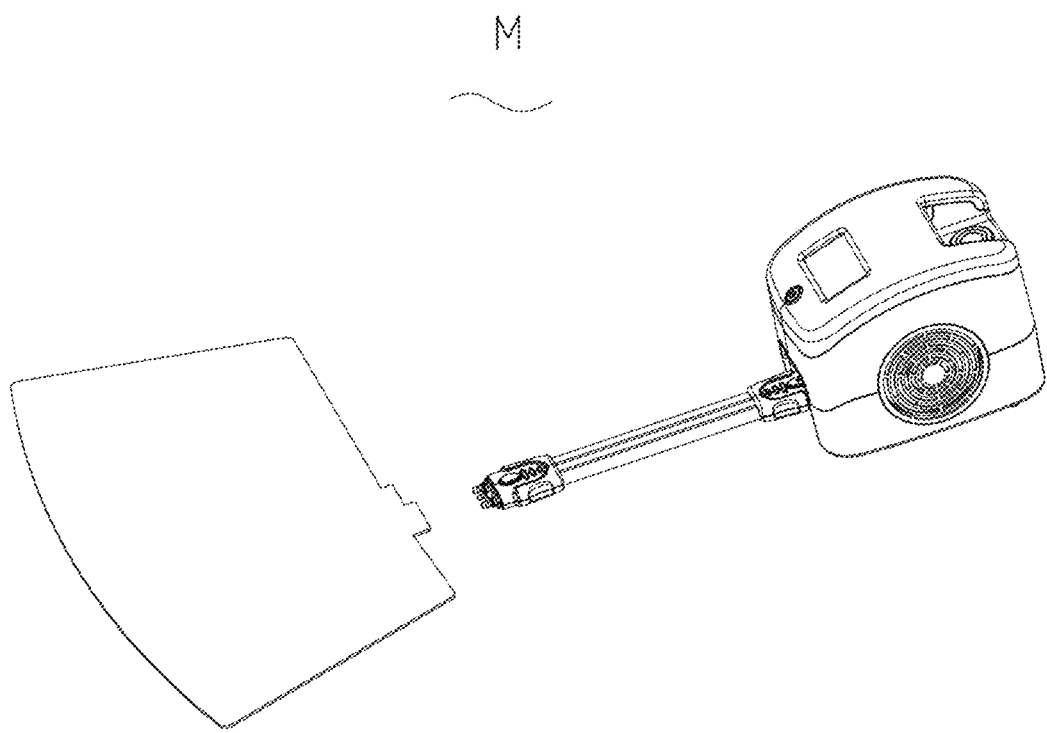
FIG. 18 is a first schematic structural diagram of a portable device for cold therapy with optional heat and compression therapy according to an embodiment of the present disclosure.

In one embodiment, referring to FIG. 15, the heat exchanger 15 includes a second cooling plate 153, and the second cooling plate 153 is placed underneath the reservoir 12. The second cooling plate 153 is provided with a second air inlet 1531 and a second air outlet 1532, the second air inlet 1531 is connected to the first tube 171, and the second air outlet 1532 is connected to the second tube 172. The reservoir 12 includes a heat-conducting material.

It should be noted that both the reservoir 12 and the second cooling plate 153 include copper materials. Gas enters the second cooling plate 153 underneath the reservoir 12 through the first tube 171 and the second air inlet 1531 and then exits through the second air outlet 1532 and the second tube 172, so that the second cooling plate 153 is cooled, and the reservoir 12 is integrally cooled through the second cooling plate 153, thereby reducing the temperature of the liquid in the reservoir 12. The second cooling plate 153 and the reservoir 12 may be integrally formed or may be separately placed.

In one embodiment, the heat exchanger 15 includes one or more combinations of the first cooling plate 151, the spiral tube 152, and the second cooling plate 153.

It should be noted that the first cooling plate 151, the spiral tube 152 or the second cooling plate 153 are cooled after the gas enters the first cooling plate 151, the spiral tube 152 or the second cooling plate 153 through the first tube 171, so that the temperature of the liquid in the reservoir 12 is reduced.

In one embodiment, a liquid level detector 61 and a temperature sensor 62 are further provided in the reservoir 12, and the liquid level detector 61 and the temperature sensor 62 are both electrically connected to the control assembly.

It should be noted that the liquid level detector 61 is placed in the reservoir 12 for detecting a height of a liquid position. The temperature sensor 62 is placed on the side of the reservoir 12 for detecting temperature of the liquid in the reservoir 12, to control the temperature by means of the control assembly to achieve a suitable cold compression or hot compression effect.

In one embodiment, the second tube 172 includes a capillary tube section, and the capillary tube section is placed between the heat exchanger 15 and the condenser 13.

It should be noted that the second tube 172 includes a second tube connecting section extending out of the heat exchanger 15 to connect the condenser 13, and a condenser section. The capillary tube section is placed on the second tube connecting section extending out of the heat exchanger 15 to connect the condenser 13. The second tube connecting section extends out of the heat exchanger 15 with a tendency of reduced tube diameter to form the capillary tube section. Preferably, the diameter is reduced to 0.2 times the diameter of the original tube (i.e., the second tube connecting section).

It should be noted that, after the gas used as the cooling agent passes through the capillary tube section with a small diameter, a flowing speed of the gas becomes slow due to a small sectional area of the capillary tube section, so that pressure of the gas is reduced, and meanwhile, the temperature of the gas is reduced. At this point, high-temperature and high-pressure gas just output from the heat exchanger 15 is able to be depressurized through the capillary tube section.

In one embodiment, the condenser 13 includes a heat conduction tube, and the heat conduction tube is U-shaped and is bent along an inner wall of the condenser 13. One end of the heat conduction tube extends out of the condenser 13 to be connected to the capillary tube section, and the other end of the heat conduction tube extends out of the condenser 13 to be connected to the compressor 11.

It should be noted that the heat conduction tube includes a copper tube. The gas enters the condenser section after being depressurized through the capillary tube section, and the condenser section is provided with a copper tube. Heat of the gas is absorbed and gradually dissipated into surrounding environment by using the copper tube. Meanwhile, the working surface of the fan 14 faces a position of the copper tube in the condenser 13, further enhancing heat dissipation of the gas. The gas subjected to heat dissipation through the copper tube and the fan 14 is conveyed back to the compressor 11 through the third tube 173.

In one embodiment, a water pump 21 is further provided, the first liquid outlet of the reservoir 122 is connected to a third liquid inlet A1 of the first body wrap A through the water pump 21, and the water pump 21 is electrically connected to the control assembly. In response to the water pump 21 working, the liquid in the reservoir 12 flows into the first body wrap A through the first liquid outlet of the reservoir 122 and the third liquid inlet A1, and the liquid in the first body wrap A flows back into the reservoir 12 through a third liquid outlet A2 of the first body wrap and the first liquid inlet of the reservoir 121.

Figure 7:
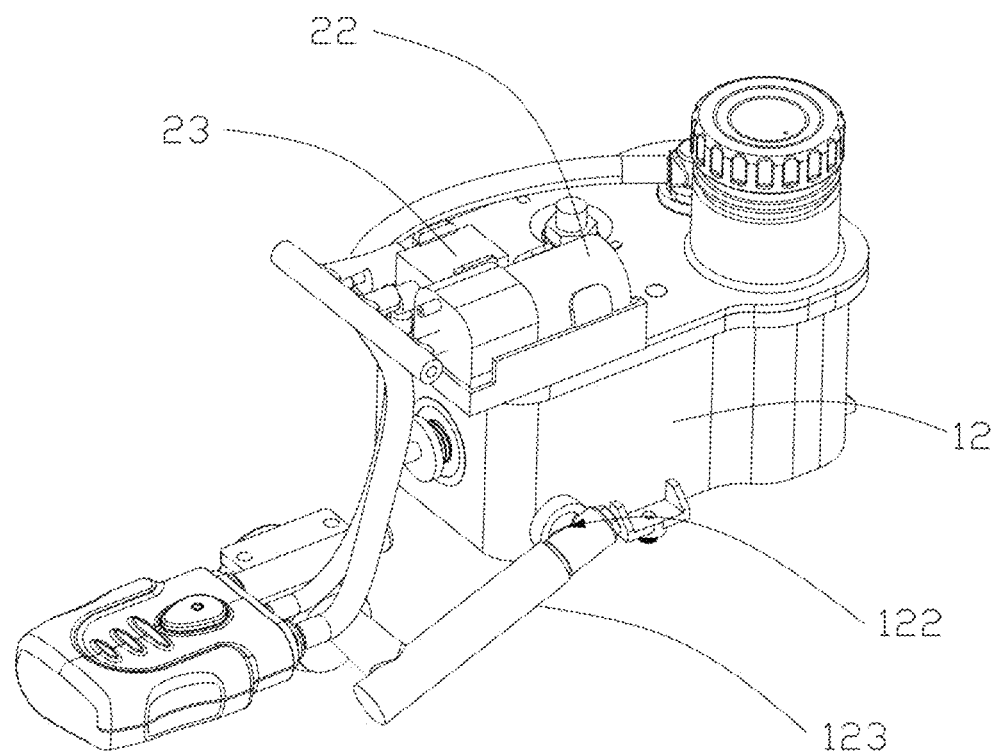
FIG. 7 is a third schematic structural diagram of a portable system for cold therapy with optional heat and compression therapy according to an embodiment of the present disclosure.

It should be noted that, referring to FIG. 7, the first liquid inlet of the reservoir 121 is connected to a first adapter, and the first liquid outlet of the reservoir 122 is connected to a second adapter 123. The first adapter and the second adapter 123 are respectively configured to connect the liquid tube. The liquid in the reservoir 12 flows out of the first liquid outlet of the reservoir 122 and then flows into the first body wrap A after being pressurized by the water pump 21.

Figure 10:
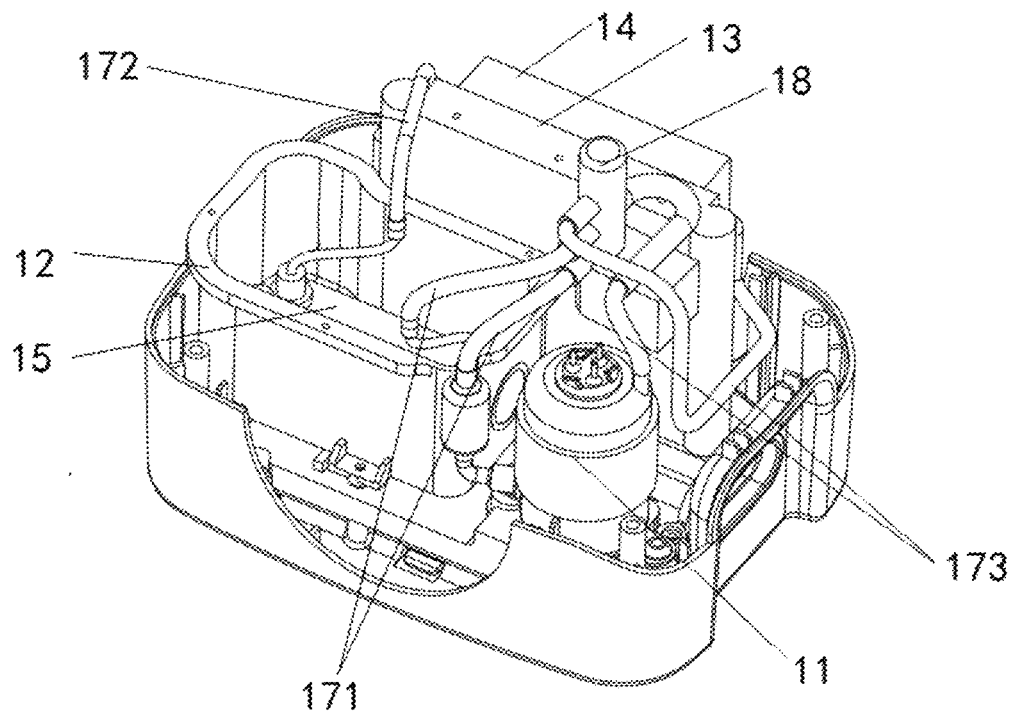
FIG. 10 is a sixth schematic structural diagram of a portable system for cold therapy with optional heat and compression therapy according to an embodiment of the present disclosure.

In one embodiment, referring to FIG. 10, a four-way valve 18 is further provided. The compressor 11 is connected to the four-way valve 18 and then to the heat exchanger 15 through the first tube 171. The condenser 13 is connected to the four-way valve 18 and then to the compressor 11 through the third tube 173. The four-way valve 18 is electrically connected to the control assembly, and the four-way valve 18 is controlled by the control assembly to change a gas flow direction. In some examples, the gas in the compressor 11 passes through the condenser 13 first and then through the heat exchanger 15. In some examples, the gas in the compressor 11 passes through the heat exchanger 15 first and then through the condenser 13 to achieve a heating effect.

It should be noted that the heat exchanger 15 may be the first cooling plate 151, the spiral tube 152, or the second cooling plate 153. The control assembly controls the passage inside the four-way valve 18. In some examples, the control assembly cause liquefied gas in the compressor 11 to first pass through the condenser 13. In the condenser 13, the liquefied gas absorbs heat, gasifies, and the temperature of the gas increases. The gas with increased temperature then releases heat as it passes through the heat exchanger 15, subsequently raising the temperature of the liquid inside the reservoir 12. The gas, after being cooled, returns to the compressor 11. In some examples, the control assembly cause the high temperature and high-pressure refrigerant gas in the compressor 11 passes through the heat exchanger 15 first, and the high temperature and high pressure refrigerant gas dissipates and liquefies in the heat exchanger 15, subsequently raising the temperature of the liquid inside the reservoir 12. The refrigerant liquid passes through the capillary tube section and then passes through the condenser 13 to evaporate and gasify, and the refrigerant gas returns to the compressor 11. By providing the four-way valve 18, only one heat exchanger 15 needs to be provided to cool or heat the liquid, thereby reducing component settings (such as a heating tube 16) and saving costs.

In one embodiment, referring to FIG. 12 to FIG. 14, a heating mechanism is further provided, and the heating mechanism includes a heating tube 16. The heating tube 16 is placed inside the reservoir 12 and is electrically connected to the control assembly.

It should be noted that, when the liquid in the reservoir 12 needs to be heated, the compressor 11, the condenser 13 and the fan 14 are controlled to pause by the control assembly, and the heating tube 16 is activated by the control assembly to increase the temperature of the liquid in the reservoir 12. The liquid with increased temperature flows into the first body wrap A through the liquid inlet of the first body wrap, providing the first body wrap A with a hot compression function. The body wrap heating mechanism is controlled by the control assembly to increase the temperature of the liquid in the reservoir 12. In some examples, a heating rate is such that the liquid reaches 43° C. from room temperature within about 6 minutes, a heating power is about 150 watts, and the achieved heating capacity is about 150 watts, thus having excellent heating effects, high efficiency, and stability. In some examples and referring to FIG. 29, under the condition of the ambient temperature of 25-28° C., with an area of 1 m$^2$ of the first body wrap A, a heating rate is such that the surface temperature of the first body wrap A reaches 43° C. within about 8 minutes, a heating power is about 150 watts, and the achieved heating capacity is about 150 watts, thus having excellent heating effects, high efficiency, and stability.

In one embodiment, a first air pump 22, a first solenoid valve 23, and a first air tube 174 are further provided. The first air pump 22 is connected to the first body wrap A through the first air tube 174, and the first solenoid valve 23 is arranged on the first air tube 174. The first air pump 22 and the first solenoid valve 23 are both electrically connected to the control assembly. The first body wrap A is inflated by the first air pump 22, and the first body wrap A is deflated by the first solenoid valve 23.

It should be noted that, referring to FIG. 2, FIG. 6 and FIG. 7, the first air pump 22 and the first solenoid valve 23 may be placed at the top of the reservoir 12. Alternatively, referring to FIG. 3 and FIG. 8, the first air pump 22 and the first solenoid valve 23 may be placed in front of the reservoir 12 and located at the side of the compressor 11. The air entering the first air tube 174 is pressurized by the first air pump 22 to be conveyed into the first body wrap A, so that the first body wrap A is inflated. In addition, the first solenoid valve 23 is a two-way solenoid valve and the first body wrap A is deflated by the first solenoid valve 23. On the one hand, the first body wrap A is expanded by inflation, allowing the first body wrap A to conform more closely to therapy areas, thereby enhancing the therapy effect of the cold therapy with optional heat and compression therapy. On the other hand, the combination of inflation and deflation allows the first body wrap A to provide medical effects such as massage and compression.

In one embodiment, a second air pump 24, a second solenoid valve 25, a third solenoid valve 26, a second air tube 175, and a third air tube 176 are further provided. The second air pump 24 is connected to the second body wrap B through the second air tube 175, and the second solenoid valve 25 is arranged on the second air tube 175; the second air pump 24 is connected to the third body wrap C through the third air tube 176, and the third solenoid valve 26 is arranged on the third air tube 176. The second air pump 24, the second solenoid valve 25, and the third solenoid valve 26 are all electrically connected to the control assembly. The second body wrap B and the third body wrap C are inflated by the second air pump 24, the second body wrap B is deflated by the second solenoid valve 25, and the third body wrap C is deflated by the third solenoid valve 26.

Figure 4:
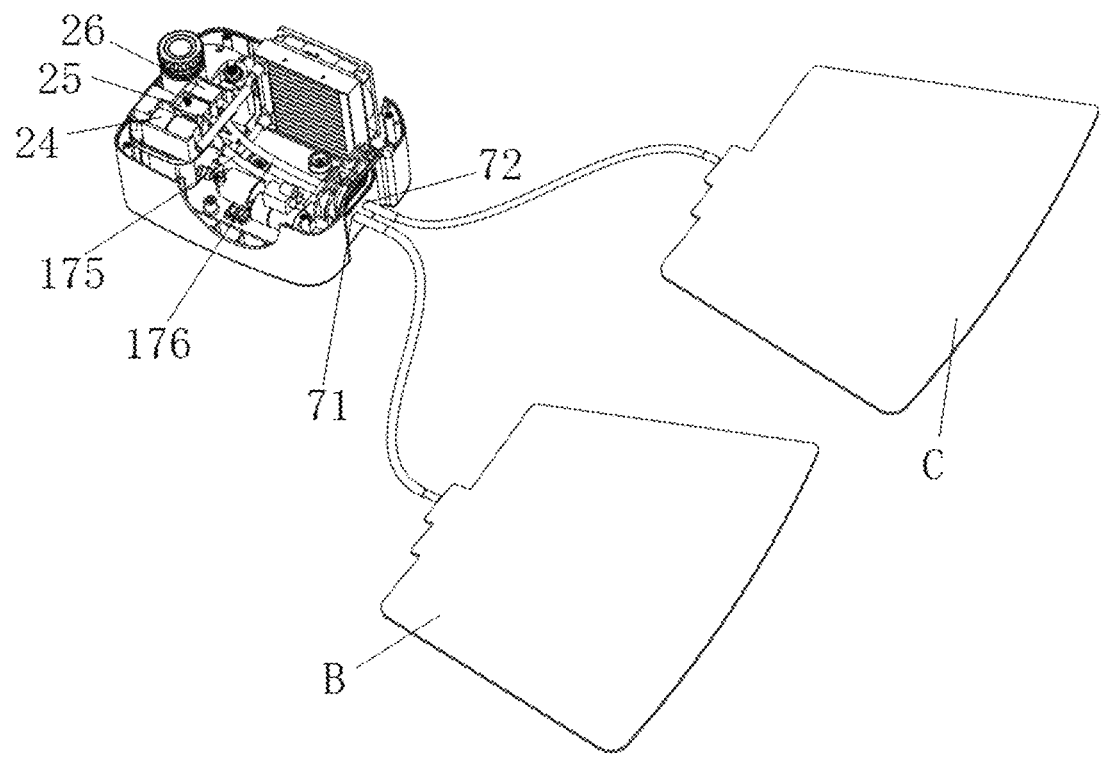
FIG. 4 is a third schematic structural diagram of a portable device for cold therapy with optional heat and compression therapy according to an embodiment of the present disclosure.
Figure 5:
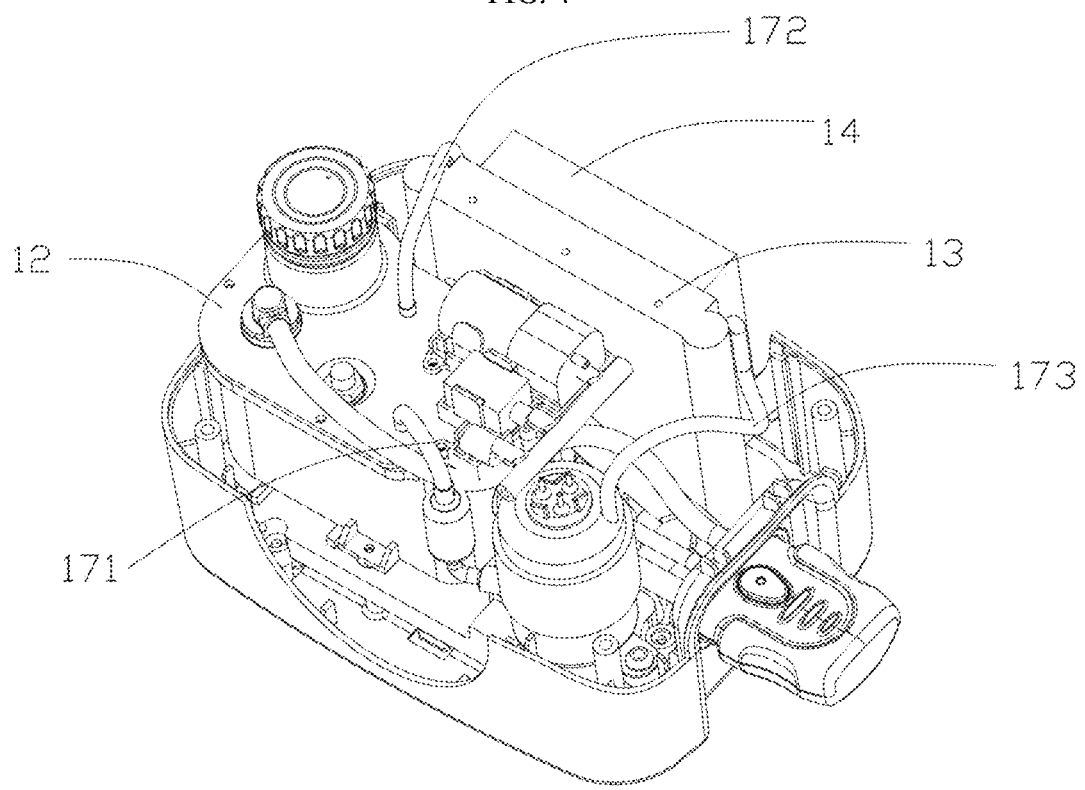
FIG. 5 is a first partial schematic structural diagram of a portable system for cold therapy with optional heat and compression therapy according to an embodiment of the present disclosure.
Figure 8:
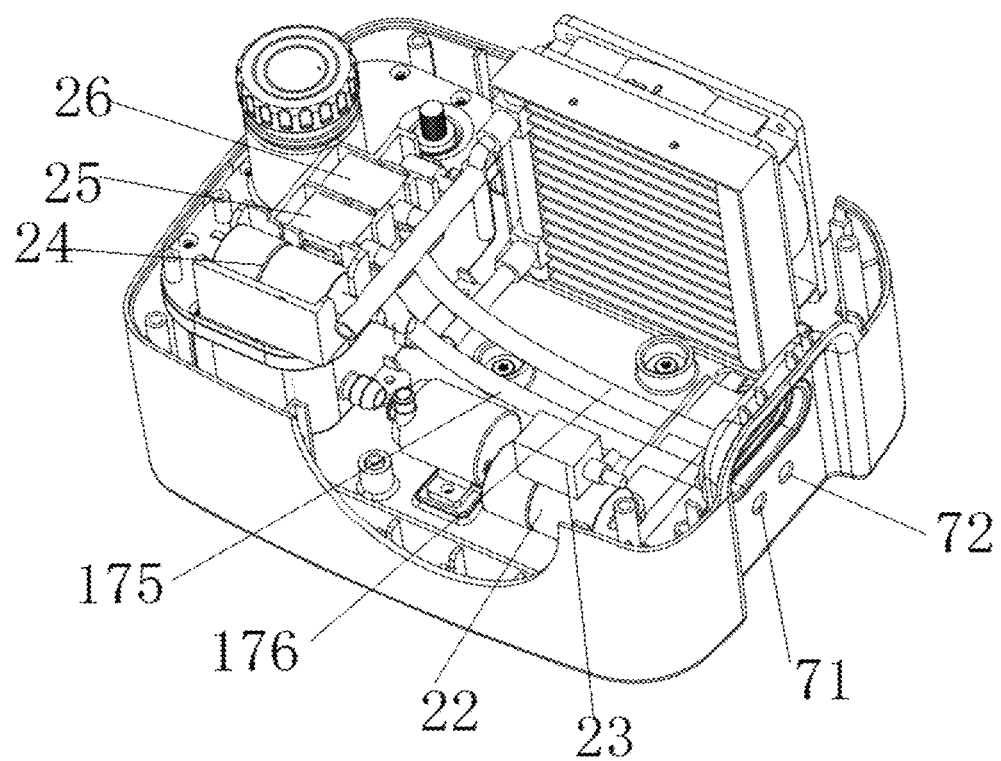
FIG. 8 is a fourth schematic structural diagram of a portable system for cold therapy with optional heat and compression therapy according to an embodiment of the present disclosure.
Figure 9:
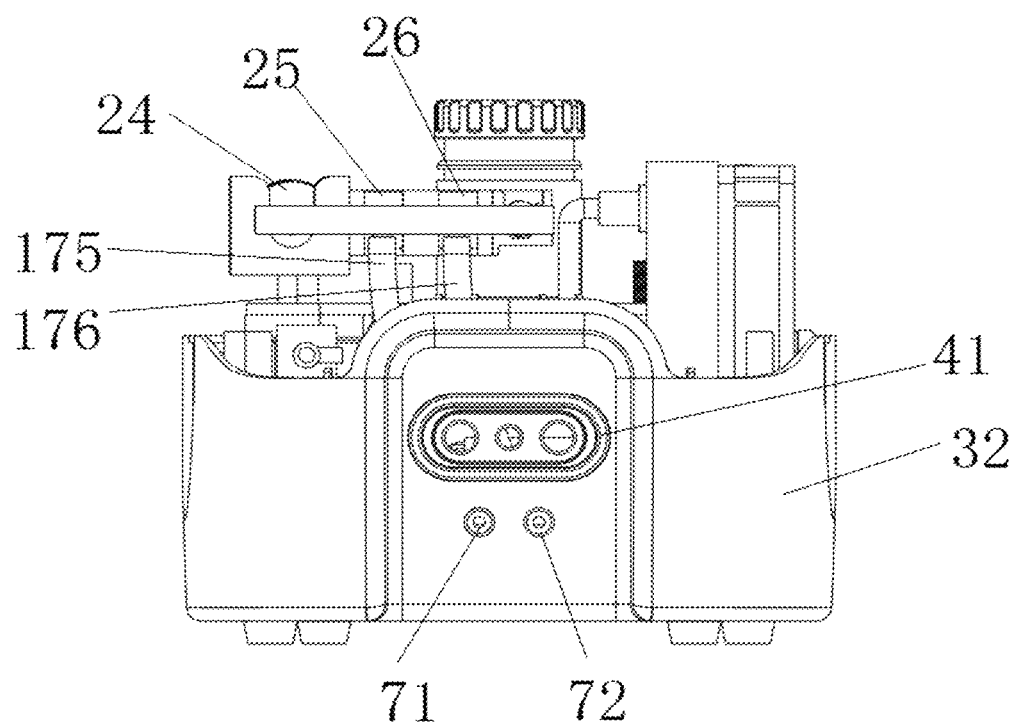
FIG. 9 is a fifth schematic structural diagram of a portable system for cold therapy with optional heat and compression therapy according to an embodiment of the present disclosure.

It should be noted that, referring to FIG. 4, FIG. 8, FIG. 9, the second air pump 24, the second solenoid valve 25, and the third solenoid valve 26 are placed at the top of the reservoir 12, and the first air pump 22 and the first solenoid valve 23 are placed in front of the reservoir 12. When a user only needs an air pressure function, the body wraps are communicated with the second air tube 175 and/or the third air tube 176. The air entering the second air tube 175 is pressurized by the second air pump 24 and then conveyed into the second body wrap B, and the air entering the third air tube 176 is pressurized by the second air pump 24 and then conveyed into the third body wrap C, so that the second body wrap B and the third body wrap C are inflated. In addition, the second solenoid valve 25 and the third solenoid valve 26 are three-way solenoid valves. The second body wrap B is deflated by the second solenoid valve 25, and the third body wrap C is deflated by the third solenoid valve 26. The combination of inflation and deflation allows the second body wrap B and the third body wrap C to provide medical effects such as massage and compression. The device may simultaneously connect the first body wrap A, the second body wrap B, and the third body wrap C for use by three users at the same time, achieving a high utilization rate of the device.

In one embodiment, a housing, a bracket 31 and a connector 41 are provided. The housing includes a bottom shell 32, an upper shell 33, and a surface cover 34. The bracket 31 is embedded in the housing, and the reservoir 12 is placed on the bracket 31. An avoidance portion is provided on the bracket, and the condenser 13 is embedded in the avoidance portion. A first groove 321 is formed on an exterior side of the bottom shell 32. One end of the connector 41 is inserted into the first groove 321 to respectively connect to the first liquid outlet of the reservoir 122, the first liquid inlet of the reservoir 121 and the first air tube 174. The other end of the connector 41 is configured to be connected to a plurality of tubes, enabling the first liquid outlet of the reservoir 122, the first liquid inlet of the reservoir 121 and the first air tube 174 to be respectively connected to the first body wrap A.

Referring to FIG. 8 and FIG. 9, the bottom shell 32 is further provided with a first air hole 71 and a second air hole 72, and the first air hole 71 and the second air hole 72 are placed below the first groove 321. One side of the first air hole 71 is connected to the second air tube 175, and one side of the second air hole 72 is connected to the third air tube 176. The other side of the first air hole 71 and the other side of the second air hole 72 are configured to be connected to tubes, enabling the second air tube 175 to be connected to the second body wrap B and the third air tube 176 to be connected to the third body wrap C.

It should be noted that the bracket 31 is placed at the top of the bottom shell 32 in the housing. The bracket 31 is placed on a side of the bottom shell 32 facing the reservoir 12.

It should be noted that a dust cover 35 is provided at a position, relative to the fan 14, on the side of the housing to prevent dust and dirt from entering the interior of the fan 14.

It should be noted that a connector base 42 is placed at the first groove, and the connector base 42 is configured to detachably connect the connector 41 to the bottom shell 32.

In one embodiment, the control assembly includes a main control board 51 (e.g., a circuit board), a display screen 52, and a battery 53. The display screen 52 and the battery 53 are electrically connected to the main control board 51. The display screen 52 is placed on the surface cover 34. An exterior side of the bottom shell 32 facing the bracket 31 is recessed to form a second groove 322, and the battery 53 is placed in the second groove 322. The battery includes a storage battery.

It should be noted that the main control board 51 is controlled through the display screen 52, working temperature of the first body wrap A is able to be set, air pressure values of the first body wrap A, the second body wrap B and the third body wrap C are able to be set, and the pressing effect is achieved by adjusting the inflation and deflation.

It should be noted that the battery 53 is rechargeable, which is convenient in the absence of alternating current. For example, the device in the present disclosure is also able to work normally when outdoors, which is convenient for users to use. Furthermore, the battery 53 is able to be detached from the second groove 322, which is convenient for charging and storage.

In some examples, referring to FIG. 1 to FIG. 10, FIG. 11, FIG. 14, FIG. 15, FIG. 28, and FIG. 29, the present disclosure provides a portable system for cold therapy with optional heat and compression therapy, applied to a first body wrap A, including a cooling mechanism, a reservoir 12, and a control assembly; wherein the cooling mechanism comprises a compressor 11, a condenser 13, a fan 14, and a heat exchanger 15, and the control assembly is electrically connected to the compressor 11, the condenser 13, and the fan 14, respectively; and wherein: the compressor 11, the condenser 13, and the fan 14 are placed outside the reservoir 12; the heat exchanger 15 is placed inside or underneath the reservoir 12, and is in direct or indirect contact with liquid in the reservoir 12 to cool the liquid; the compressor 11 has an air inlet connected to the heat exchanger 15 through a first tube 171; the heat exchanger 15 is connected to the condenser 13 through a second tube 172; the condenser 13 is connected to an air outlet of the compressor 11 through a third tube 173; the first tube 171 and the second tube 172 are connected by fluid, and the second tube 172 and the third tube 173 are connected by fluid, enabling refrigerant gas in the compressor 11 to pass through the condenser 13 first and then through the heat exchanger 15 to achieve a cooling effect; the fan 14 has a working surface facing the condenser 13; and the reservoir 12 comprises a first liquid inlet of the reservoir 121 and a first liquid outlet of the reservoir 122; wherein the liquid in the reservoir 12 flows into the first body wrap A through the first liquid outlet of the reservoir 122, and liquid in the first body wrap A flows into the reservoir 12 through the first liquid inlet of the reservoir 121.

It should be noted that the compressor 11, the condenser 13, the fan 14 and the heat exchanger 15 can all be one or more. A plurality of the compressors 11 are arranged in series. A plurality of the condenser 13 are arranged in series, each working face of the fan 14 is toward the condenser 13. A plurality of the heat exchangers 15 are arranged in series.

In one embodiment, the heat exchanger 15 is placed inside the reservoir 12, referring to FIG. 11, the heat exchanger 15 comprises a first cooling plate 151; wherein the first cooling plate 151 comprises a first air inlet of the first cooling plate 1512 and a first air outlet of the first cooling plate 1511; and wherein the first air outlet of the first cooling plate 1511 is connected to the first tube 171, and the first air inlet of the first cooling plate 1512 is connected to the second tube 172.

It should be noted that the first cooling plate 151 includes a brazed plate heat exchanger. The refrigerant liquid enters the brazing plate heat exchanger in the reservoir 12 through the second tube 172 and the first air inlet of the first cooling plate 1512, and then goes out through the first tube 171 to cool the brazing plate heat exchanger, and then the liquid temperature in the reservoir 12 decreases through the brazing plate heat exchanger.

In one embodiment, the heat exchanger 15 is placed inside the reservoir 12, referring to FIG. 14, the heat exchanger 15 comprises a spiral tube 152; wherein the spiral tube 152 has one end connected to the first tube 171 and another end connected to the second tube 172.

It should be noted that the spiral tube 152 includes a copper material or a stainless-steel material. Refrigerant liquid enters the spiral tube 152 in the reservoir 12 through the second tube 172 and then exits through the third tube 171, so that the spiral tube 152 is cooled, and then the temperature of the liquid in the reservoir 12 is reduced through the spiral tube 152. The spiral structure of the spiral tube 152 enables refrigerant conveyed by the compressor 11 to stay in the spiral tube 152 for a longer time and increases a contact area between the spiral tube 152 with the liquid in the reservoir 12, so as to perform sufficient heat exchange with the liquid, thereby improving the cooling efficiency during cold therapy.

In one embodiment, the heat exchanger 15 is placed underneath the reservoir 12, referring to FIG. 15, the heat exchanger 15 comprises a second cooling plate 153; wherein the second cooling plate 153 is provided with a second air inlet of the second cooling plate 1532 and a second air outlet of the second cooling plate 1531, the second air outlet of the second cooling plate 1531 is connected to the first tube 171, and the second air inlet of the second cooling plate 1532 is connected to the second tube 172; and wherein the reservoir 12 comprises a heat-conducting material.

It should be noted that both the reservoir 12 and the second cooling plate 153 include copper materials. Refrigerant liquid enters the second cooling plate 153 underneath the reservoir 12 through the second tube 172 and the second air inlet of the second cooling plate 1532 and then exits through the second air outlet of the second cooling plate 1531 and the first tube 171, so that the second cooling plate 153 is cooled, and the reservoir 12 is integrally cooled through the second cooling plate 153, thereby reducing the temperature of the liquid in the reservoir 12. The second cooling plate 153 and the reservoir 12 may be integrally formed or may be separately placed.

In one embodiment, the heat exchanger 15 includes one or more combinations of the first cooling plate 151, the spiral tube 152, and the second cooling plate 153.

It should be noted that the first cooling plate 151, the spiral tube 152 or the second cooling plate 153 are cooled after the refrigerant liquid enters the first cooling plate 151, the spiral tube 152 or the second cooling plate 153 through the second tube 172, so that the temperature of the liquid in the reservoir 12 is reduced.

The technical problems to be solved in the embodiments lie in insufficient cooling effect and low efficiency of the cooling mechanism. The portable system for cold therapy with optional heat and compression therapy according to the present disclosure has the following beneficial effects.

In a first aspect, the cooling mechanism is equipped with the compressor 11, the condenser 13, the fan 14, and the heat exchanger 15. High temperature and high-pressure refrigerant gas is transported from the compressor 11 to the condenser 13 through the third tube 173, at this time, the temperature of the refrigerant gas is high, and the fan 14 is utilized to cool the refrigerant gas in the condenser 13, and the refrigerant gas is liquefied. Refrigerant liquid is transported from the condenser 13 to the heat exchanger 15 through the second tube 172. In the heat exchanger 15, the refrigerant liquid undergoes heat exchange with the liquid in the reservoir 12, absorbs heat from the liquid and gasifies, and the liquid temperature decreases. Refrigerant gas is transported from the heat exchanger 15 to the compressor 11 through the first tube 171, and the compressor 11 compresses the refrigerant gas. This process circulates to cool the liquid in the reservoir 12, the liquid with decreased temperature flows into the first body wrap A through the third liquid inlet A1, providing the first body wrap A with a cold compression function. Referring to FIG. 28, under the condition of the ambient temperature of 25-28° C., with an area of 1 $m^2$ of the first body wrap A, a cooling rate is such that the surface temperature of the first body wrap A reaches 5° C. within about 10 minutes, a cooling power is about 75 watts, and the achieved cooling capacity is about 250 watts. The system exhibits excellent cooling effects, high efficiency, stability, and low power consumption.

In a second aspect, the first air pump 22 and the first solenoid valve 23 are provided to inflate the first body wrap A, allowing the first body wrap A to conform more closely to therapy areas. This enhances the therapy effect of the cold therapy with optional heat and compression therapy. Additionally, the combination of inflation and deflation allows the first body wrap A to provide medical effects such as massage and compression. The system can be connected to the first body wrap A, the second body wrap B, the third body wrap C for the use of three users at the same time, high utilization rate of equipment. The device has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir 12, which are able to directly or indirectly contact the liquid in the reservoir 12. This allows pre-cooling or pre-heating of the liquid, thereby enabling immediate use when the user requires therapy.

In some embodiments, further comprises a housing, a bracket, and a connector, and wherein: the housing comprises a bottom shell, an upper shell and a surface cover, the bracket is embedded in the housing, and the reservoir is placed on the bracket; an avoidance portion is displayed on the bracket, wherein the condenser is embedded in the avoidance portion; an exterior side of the bottom shell is provided with a first groove, wherein the connector has one end inserted into the first groove and respectively connected to the first liquid outlet, the first liquid inlet, and a first air tube, and has another end configured to be connected to a plurality of tubes, enabling the first liquid outlet, the first liquid inlet and the first air tube to be respectively connected to the first body wrap; and the bottom shell is further provided with a first air hole and a second air hole, wherein the first air hole and the second air hole are placed below the first groove; and wherein one side of the first air hole is connected to a second air tube, one side of the second air hole is connected to a third air tube, and another side of the first air hole and another side of the second air hole are configured to be connected to tubes, enabling the second air tube to be connected to a second body wrap and the third air tube to be connected to a third body wrap.

In some embodiments, the control assembly further comprises a main control board, a display screen, and a battery; and wherein: the display screen and the battery are both electrically connected to the main control board; the display screen is placed on the surface cover; and an exterior side of the bottom shell is recessed towards the bracket to form a second groove, wherein the battery is placed in the second groove, and the battery comprises a storage battery.

In some embodiments, further comprising a four-way valve, wherein the compressor is connected to the four-way valve and then to the heat exchanger through the first tube, and the condenser is connected to the four-way valve and then to the compressor through the third tube; and wherein, the four-way valve is electrically connected to the control assembly, and the four-way valve is controlled by the control assembly to change the flow direction, enabling refrigerant gas in the compressor to pass through the heat exchanger first and then through the condenser to achieve a heating effect.

In one embodiment, further comprises a housing, a bracket 31, and a connector 41, and wherein: the housing comprises a bottom shell 32, an upper shell 33 and a surface cover 34, the bracket 31 is embedded in the housing, and the reservoir 12 is placed on the bracket 31; an avoidance portion is displayed on the bracket 31, wherein the condenser 13 is embedded in the avoidance portion; an exterior side of the bottom shell is provided with a first groove 321, wherein the connector 41 has one end inserted into the first groove 321 and respectively connected to the first liquid outlet of the reservoir 122, the first liquid inlet of the reservoir 121, and a first air tube 174, and has another end configured to be connected to a plurality of tubes, enabling the first liquid outlet of the reservoir 122, the first liquid inlet of the reservoir 121 and the first air tube 174 to be respectively connected to the first body wrap A; and the bottom shell is further provided with a first air hole 71 and a second air hole 72, wherein the first air hole 71 and the second air hole 72 are placed below the first groove 321; and wherein one side of the first air hole 71 is connected to a second air tube 175, one side of the second air hole 72 is connected to a third air tube 176, and another side of the first air hole 71 and another side of the second air hole 72 are configured to be connected to tubes, enabling the second air tube 175 to be connected to a second body wrap B and the third air tube 176 to be connected to a third body wrap C.

In one embodiment, the control assembly includes a main control board 51, a display screen 52, and a battery 53. The display screen 52 and the battery 53 are both electrically connected to the main control board 51. The display screen 52 is placed on the surface cover 34. An exterior side of the bottom shell 32 facing the bracket 31 is recessed to form a second groove 322, and the battery 53 is placed in the second groove 322. The battery includes a storage battery.

It should be noted that the main control board 51 is controlled through the display screen 52, working temperature of the first body wrap A is able to be set, air pressure values of the first body wrap A, the second body wrap B and the third body wrap C are able to be set, and the pressing effect is achieved by adjusting the inflation and deflation.

It should be noted that the battery 53 is rechargeable, which is convenient in the absence of alternating current. For example, the device in the present disclosure is also able to work normally when outdoors, which is convenient for users to use. Furthermore, the battery 53 is able to be detached from the second groove 322, which is convenient for charging and storage.

In one embodiment, referring to FIG. 10, a four-way valve 18 is further provided. The compressor 11 is connected to the four-way valve 18 and then to the heat exchanger 15 through the first tube 171. The condenser 13 is connected to the four-way valve 18 and then to the compressor 11 through the third tube 173. The four-way valve 18 is electrically connected to the control assembly, and the four-way valve 18 is controlled by the control assembly to change the flow direction, enabling refrigerant gas in the compressor 11 to pass through the heat exchanger 15 first and then through the condenser 13 to achieve a heating effect.

It should be noted that the control assembly controls the passage inside the four-way valve 18, the high temperature and high-pressure refrigerant gas in the compressor 11 passes through the heat exchanger 15 first, and the high temperature and high-pressure refrigerant gas dissipates and liquefies in the heat exchanger 15, subsequently raising the temperature of the liquid inside the reservoir 12. The refrigerant liquid passes through the capillary tube section and then passes through the condenser 13 to evaporate and gasify, and the refrigerant gas returns to the compressor 11. By providing the four-way valve 18, only one heat exchanger 15 needs to be provided to cool or heat the liquid, thereby reducing component settings (such as a heating tube 16) and saving costs.

In some examples, referring to FIG. 20 to FIG. 25, FIG. 30, FIG. 31, the present disclosure provides a portable system for cold therapy with optional heat and compression therapy, applied to a first body wrap A, including a cooling mechanism, a reservoir 12, and a control assembly; wherein the cooling mechanism comprises a compressor 11, a condenser 13, a fan 14, a heat exchanger 15, and the control assembly is electrically connected to the compressor 11, the condenser 13, the fan 14, respectively; and wherein: the compressor 11, the condenser 13, the fan 14, and the heat exchanger 15 are placed outside the reservoir 12, respectively; the compressor 11 has an air inlet connected to the heat exchanger 15 through a first tube 171; the heat exchanger 15 is connected to the condenser 13 through a second tube 172; the condenser 13 is connected to an air outlet of the compressor 11 through a third tube 173; the first tube 171 and the second tube 172 are connected by fluid, and the second tube 172 and the third tube 173 are connected by fluid, enabling refrigerant gas in the compressor 11 to pass through the condenser 13 first and then through the heat exchanger 15 to achieve a cooling effect; the fan 14 has a working surface facing the condenser 13.

The reservoir 12 comprises a first liquid outlet of the reservoir 122, wherein the liquid in the reservoir 12 flows into the heat exchanger 15 first through the first liquid outlet of the reservoir 122 and then flows into the first body wrap A; the liquid in the first body wrap A can flow into the heat exchanger 15 first and then flow into the first body wrap A again, or the liquid in the first body wrap A can flow back to the reservoir 12, further comprising a heating mechanism, wherein the heating mechanism is electrically connected to the control assembly.

It should be noted that the compressor 11, the condenser 13, the fan 14 and the heat exchanger 15 can all be one or more. A plurality of the compressors 11 are arranged in series. A plurality of the condenser 13 are arranged in series, each working face of the fan 14 is toward the condenser 13. A plurality of the heat exchangers 15 are arranged in series.

Figure 20:
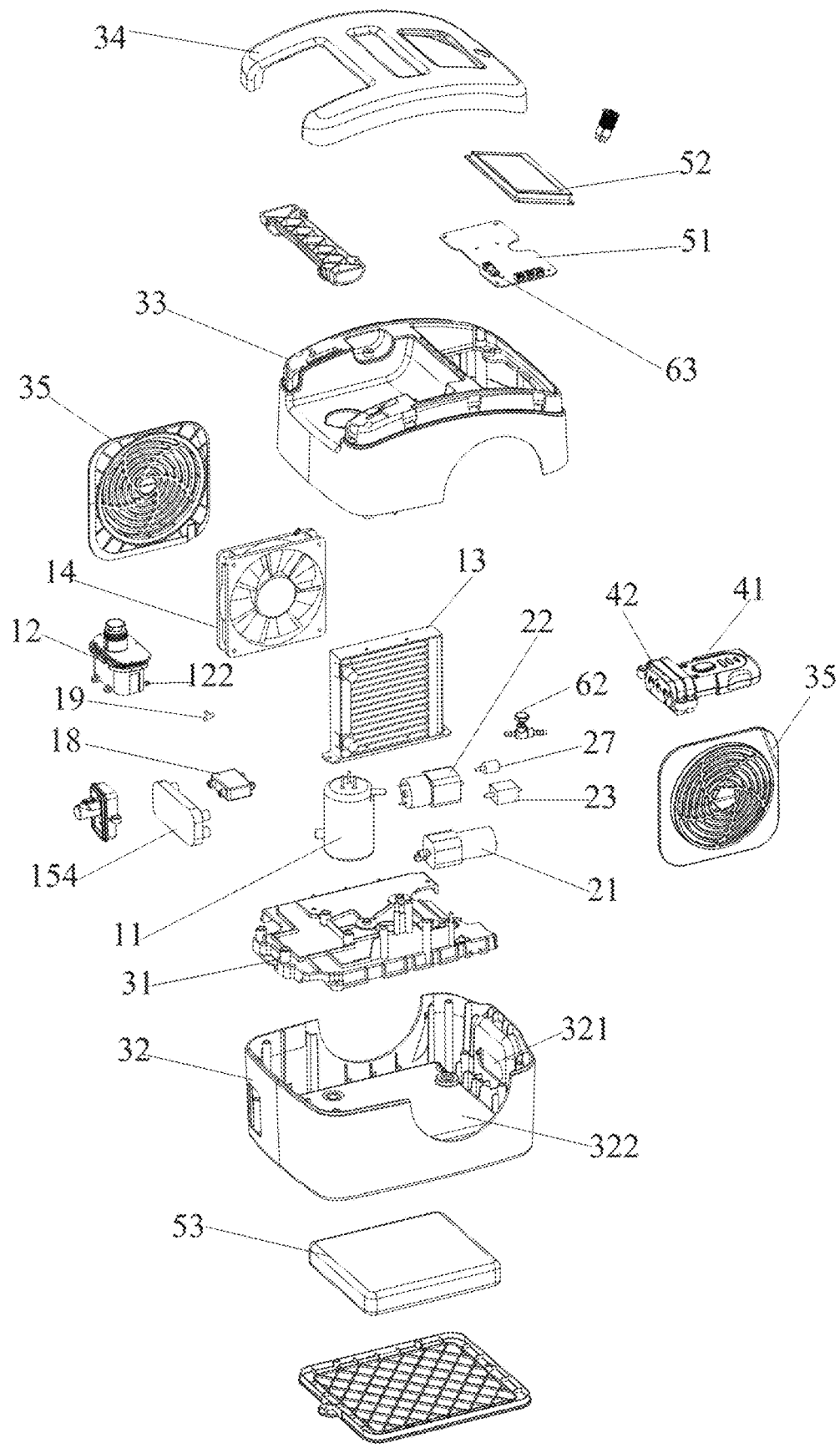
FIG. 20 is a first exploded schematic structural diagram of a portable system for cold therapy with optional heat and compression therapy according to another embodiment of the present disclosure.

In one embodiment, referring to FIG. 20, the heating mechanism comprises a four-way valve 18, wherein the compressor 11 is connected to the four-way valve 18 and then to the heat exchanger 15 through the first tube 171, and the condenser 13 is connected to the four-way valve 18 and then to the compressor 11 through the third tube 173, and the four-way valve 18 is controlled by the control assembly to change the flow direction, enabling refrigerant in the compressor 11 to pass through the heat exchanger 15 first and then through the condenser 13 to achieve a heating effect.

Figure 21:
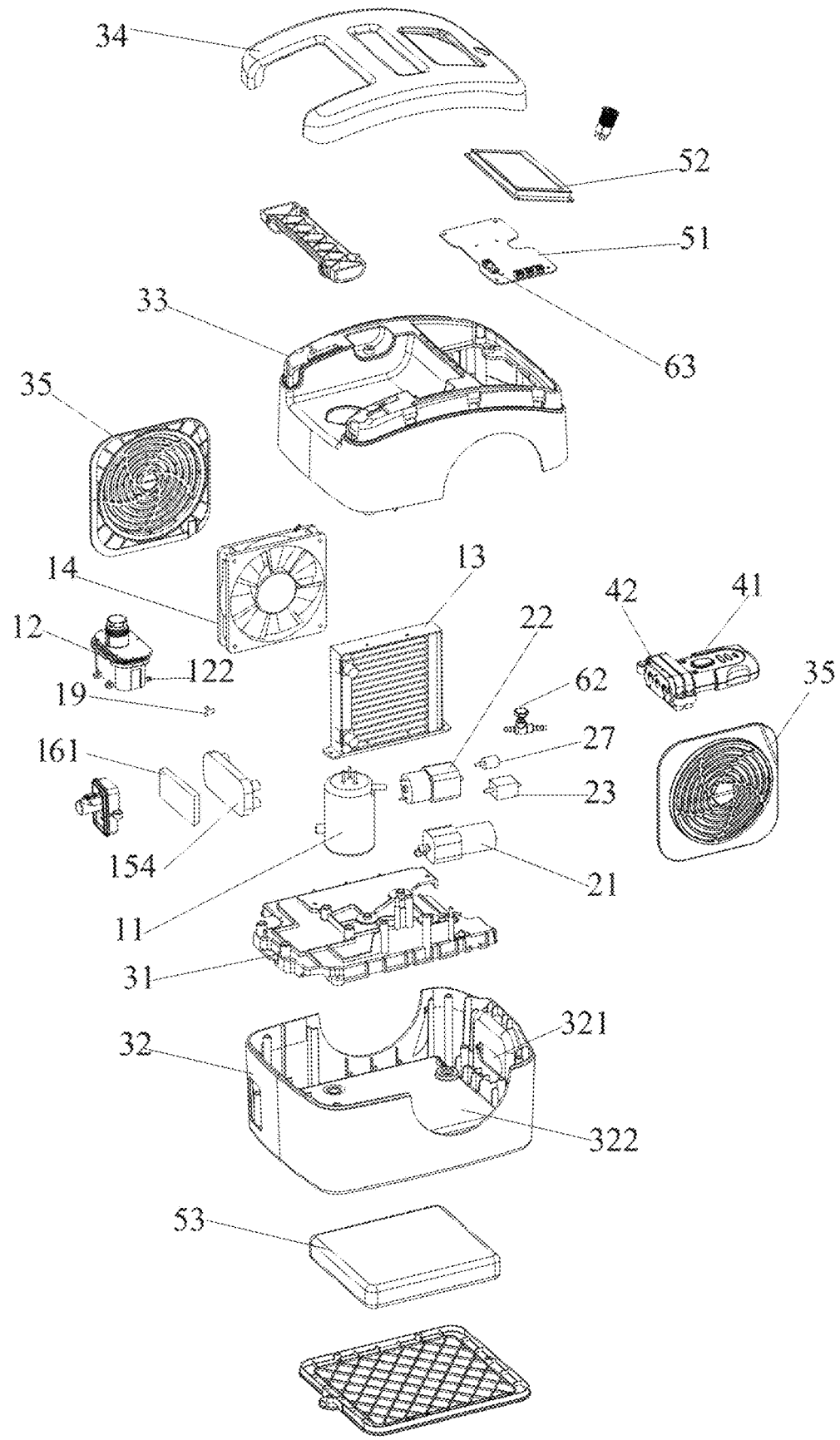
FIG. 21 is a second exploded schematic structural diagram of a portable system for cold therapy with optional heat and compression therapy according to another embodiment of the present disclosure.
Figure 22:
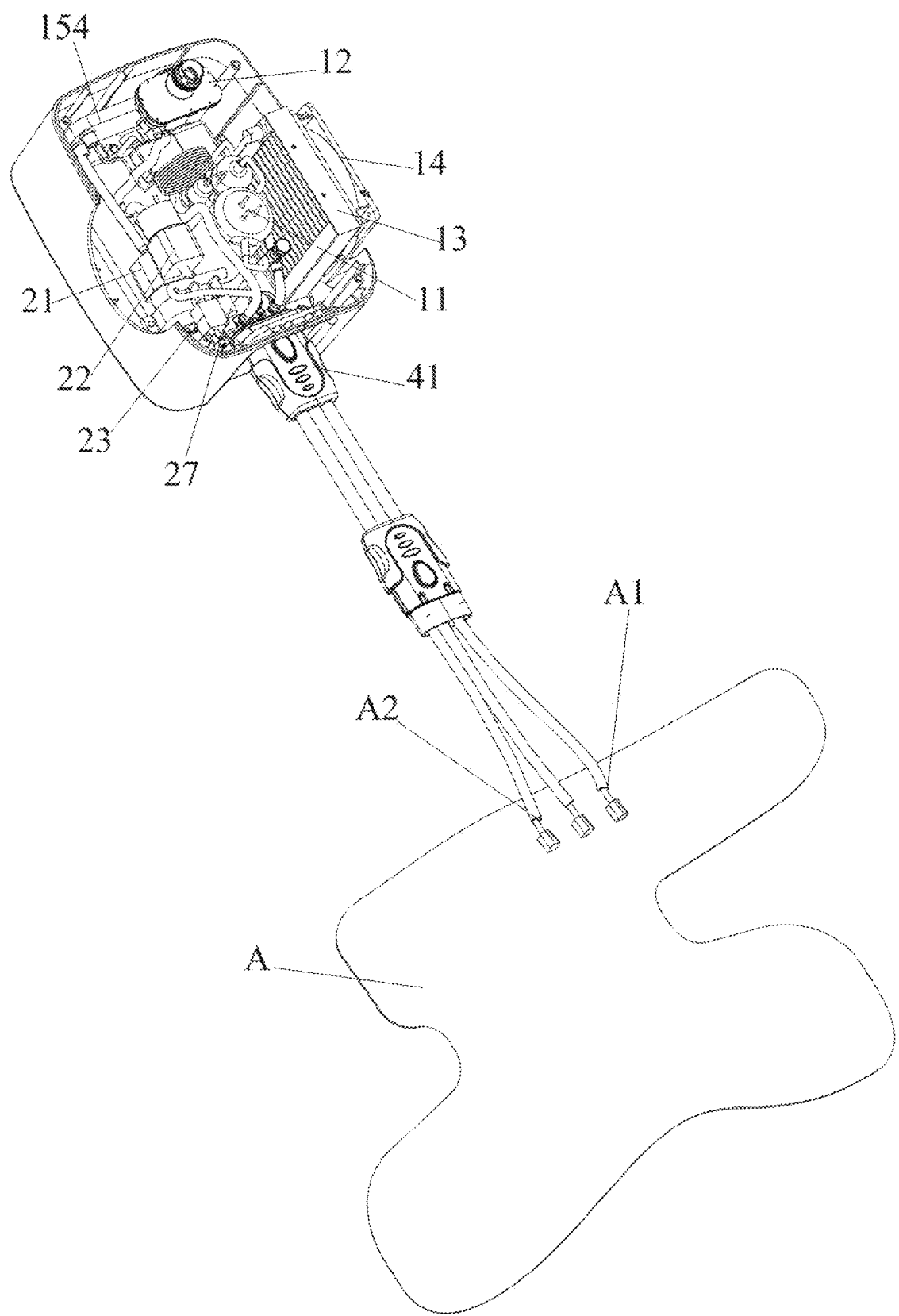
FIG. 22 is a partial schematic structural diagram of a portable device for cold therapy with optional heat and compression therapy in a manner of the heat exchanger being a third cooling plate manner.

In one embodiment, referring to FIG. 21, the heating mechanism comprises one or more heating sheets 161, the one or more heating sheets 161 are arranged on the outside of the heat exchanger 15.

It should be noted that the liquid includes water, alcohol, antifreezing solution, and the like. A concentration of 10% alcohol is preferably used.

It should be noted that a branch of the first tube 171 is provided with a refrigerant adding port, so as to maintain temperature of the cooling when the cooling mechanism works for a long time. When using the cooling mechanism in long-term circles, it may not achieve the heat exchange in an ideal state and the cooling effect cannot reach the expectation, thus the refrigerant is periodically added to improve the cooling effect.

It should be noted that the first tube 171 and the second tube 172 are connected by fluid, and the second tube 172 and the third tube 173 are connected by fluid. In fact, the first tube 171, the second tube 172 and the third tube 173 are all part of the same tube, and the same tube is connected to the compressor 11, the heat exchanger 15 and the condenser 13 to form a closed circulation loop. For example, the first tube 171 includes a compressor section, a first tube connecting section extending out of the compressor 11 to connect the heat exchanger 15, and a heat exchanger section. The second tube 172 includes a second tube connecting section extending out of the heat exchanger 15 to connect the condenser 13, and a condenser section. The third tube 173 includes a third tube connecting section extending out of the condenser 13 to connect the compressor 11.

The technical problems to be solved in the embodiments lie in insufficient cooling effect and low efficiency of the cooling mechanism.

Figure 30:
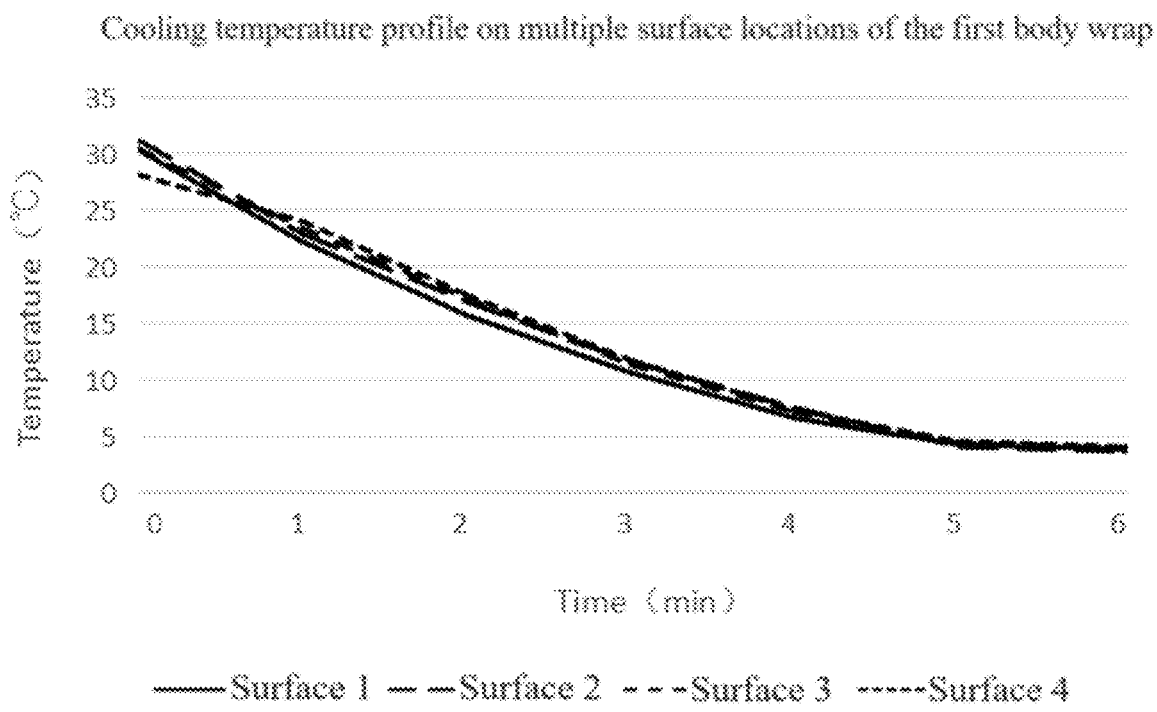
FIG. 30 is a cooling temperature profile on multiple surface locations of the first body wrap according to another embodiment of the present disclosure
Figure 31:
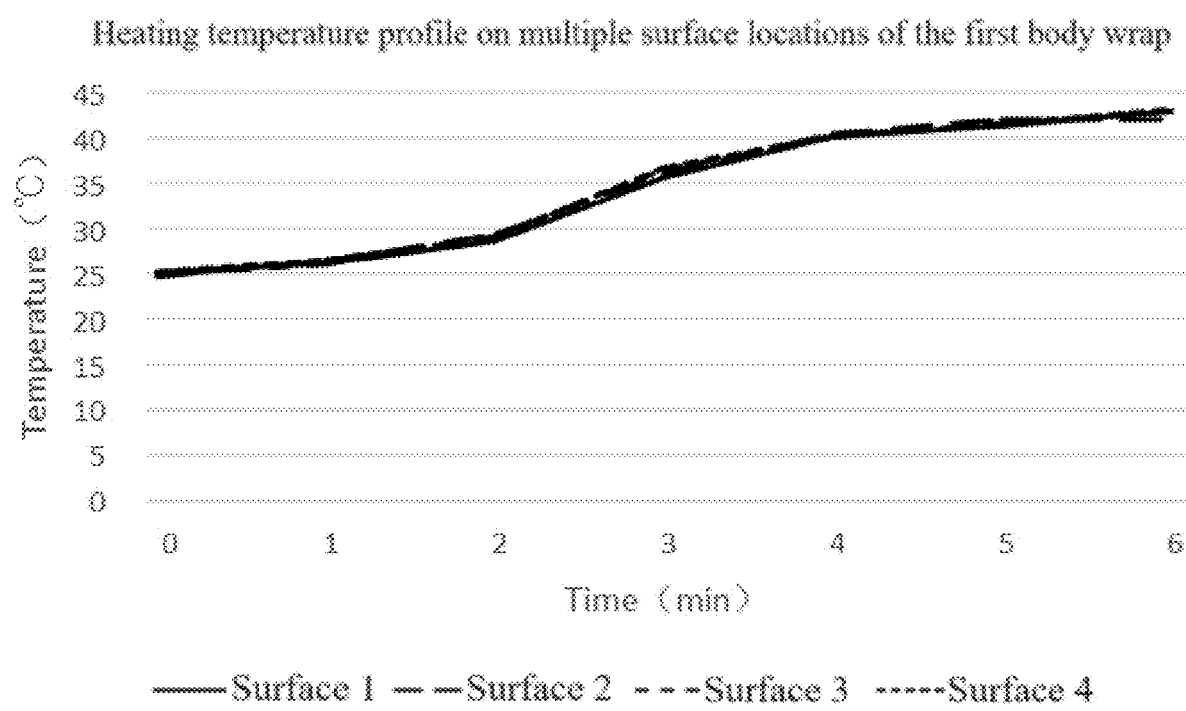
FIG. 31 is a heating temperature profile on multiple surface locations of the first body wrap according to another embodiment of the present disclosure.

The portable system for cold therapy with optional heat and compression therapy according to the present disclosure has the following beneficial effects. In a first aspect, the cooling mechanism is equipped with the compressor 11, the condenser 13, the fan 14, the heat exchanger 15. High temperature and high-pressure refrigerant gas is transported from the compressor 11 to the condenser 13 through the third tube 173, at this time, the temperature of the refrigerant gas is high, and the fan is utilized to cool the refrigerant gas in the condenser 13, and the refrigerant gas is liquefied. Refrigerant liquid is transported from the condenser 13 to the heat exchanger 15 through the second tube 172. In the heat exchanger 15, the refrigerant liquid undergoes heat exchange with the liquid in the heat exchanger 15, absorbs heat from the liquid and gasifies, and the liquid temperature decreases. Refrigerant gas is transported from the heat exchanger 15 to the compressor 11 through the first tube 171, and the compressor 11 compresses the refrigerant gas. The heat exchanger 15 is arranged on the outside of the reservoir 12, the liquid in the reservoir 12 flows into the heat exchanger 15 for cooling through the first liquid outlet of the reservoir 122 and then flows into the first body wrap A. The liquid in the first body wrap A can flow into the heat exchanger 15 for cooling again, or the liquid in the first body wrap A can flow back into the reservoir 12, providing the first body wrap A with a cold compression function, and the remaining liquid in the reservoir 12 will no longer participate in the circulation, to greatly improve the cooling efficiency, and reduce the power consumption. Referring to FIG. 30, under the condition of the ambient temperature of 25-28° C., with an area of 1 m² of the first body wrap A, a cooling rate is such that the surface temperature of the first body wrap A reaches 5° C. within about 5 minutes, a cooling power is about 75 watts, and the achieved cooling capacity is about 250 watts. The system exhibits excellent cooling effects, high efficiency, stability, and low power consumption. In a second aspect, further comprising a heating mechanism, the heating mechanism comprises a four-way valve 18 or one or more heating sheets 161, the control assembly controls the four-way valve 18 to change the flow direction or control the heating sheet heating 161, to increase the temperature of the liquid in the heat exchanger 15, the liquid with increased temperature flows into the first body wrap A through the third liquid inlet A1, providing the first body wrap A with a hot compression function. Referring to FIG. 31, under the condition of the ambient temperature of 25-28° C., with an area of 1 m² of the first body wrap A, a heating rate is such that the surface temperature of the first body wrap A reaches 43° C. within about 6 minutes, a heating power is about 75-150 watts, and the achieved heating capacity is about 75-150 watts. The device exhibits excellent heating effects, high efficiency, and stability. The cooling and heating mechanisms are simultaneously incorporated into the portable device for cold therapy with optional heat and compression therapy, provided in the present disclosure. The device has a compact, small, and lightweight structure, facilitating convenient portability. The device is versatile, offering capabilities for cold compression, hot compression, and/or massage, enhancing the user experience.

In some embodiments, further comprising a insulation device, the insulation device is arranged on the outside of the heating sheet.

In some embodiments, the heat exchanger comprises a third cooling plate; wherein the third cooling plate is provided with a third air inlet of the third cooling plate, a third air outlet of the third cooling plate, a fourth liquid inlet of the third cooling plate, and a fourth liquid outlet of the third cooling plate; wherein the third air outlet of the third cooling plate is connected to the first tube, and the third air inlet of the third cooling plate is connected to the second tube; the fourth liquid inlet of the third cooling plate is connected to the first liquid outlet of the reservoir, the fourth liquid outlet of the third cooling plate is connected to a third liquid inlet of the first body wrap, a third liquid outlet of the first body wrap is connected to the first liquid outlet of the reservoir and the fourth liquid inlet of the third cooling plate.

In some embodiments, further comprising a three-way connector, wherein the three-way connector comprises a first connector, a second connector, and a third connector; wherein the first connector is connected to the first liquid outlet of the reservoir, the second connector is connected to the fourth liquid inlet of the third cooling plate, the third connector is connected to the third liquid outlet.

In some embodiments, the first liquid outlet of the reservoir is connected to the first connector through a fifth tube, the fourth liquid inlet of the third cooling plate is connected to the second connector through a sixth tube, the fourth liquid outlet of the third cooling plate is connected to the third liquid inlet through a seventh tube, the third liquid outlet is connected to the third connector through a eighth tube; wherein the sixth tube is provided with a water pump, and the water pump is electrically connected to the control assembly; and wherein, in response to the water pump working, the liquid in the reservoir flows into the third cooling plate through the fifth tube and the sixth tube, and then flows into the first body wrap through the seventh tube; the liquid in the first body wrap flows into the third cooling plate through the eighth tube and the sixth tube, and then flows into the first body wrap again through the seventh tube; in response to the water pump stopped working, the liquid in the first body wrap flows back to the reservoir through the eighth tube and the fifth tube.

In some embodiments, the reservoir is further provided with a liquid level detector inside, the seventh tube or the eighth tube is provided with a temperature sensor, and the liquid level detector and the temperature sensor are both electrically connected to the control assembly.

In some embodiments, the second tube comprises a throttle device, and the throttle device is placed between the heat exchanger and the condenser; and wherein the condenser comprises a heat conduction tube, and the heat conduction tube has one end extending out of the condenser to be connected to the throttle device and another end extending out of the condenser to be connected to the compressor.

In some embodiments, further comprising a first air pump, a first solenoid valve, and a first air tube; wherein: the first air pump is connected to the first body wrap through the first air tube, and the first solenoid valve is arranged on the first air tube; the first air pump and the first solenoid valve are both electrically connected to the control assembly; and the first body wrap is configured to be inflated by the first air pump, and the first body wrap is configured to be deflated by the first solenoid valve.

In some embodiments, further comprising a housing, a bracket, and a connector, wherein the housing comprises a bottom shell, an upper shell and a surface cover; and wherein: the bracket is embedded in the housing, and the reservoir is placed on the bracket; an avoidance portion is displayed on the bracket, wherein the condenser is embedded in the avoidance portion; an exterior side of the bottom shell is provided with a first groove, wherein the connector has one end inserted into the first groove and respectively connected to the seventh tube, the eighth tube, and the first air tube, and has another end configured to be connected to a plurality of tubes, enabling the seventh tube, the eighth tube and the first air tube to be respectively connected to the first body wrap.

In some embodiments, the control assembly further comprises a main control board, a display screen, and a battery; and wherein: the display screen and the battery are both electrically connected to the main control board; the display screen is placed on the surface cover; and an exterior side of the bottom shell is recessed towards the bracket to form a second groove, wherein the battery is placed in the second groove, and the battery comprises a storage battery.

In one embodiment, further comprising a insulation device, the insulation device is arranged on the outside of the heating sheet 161. The insulation device may be a mica sheet.

Figure 23:
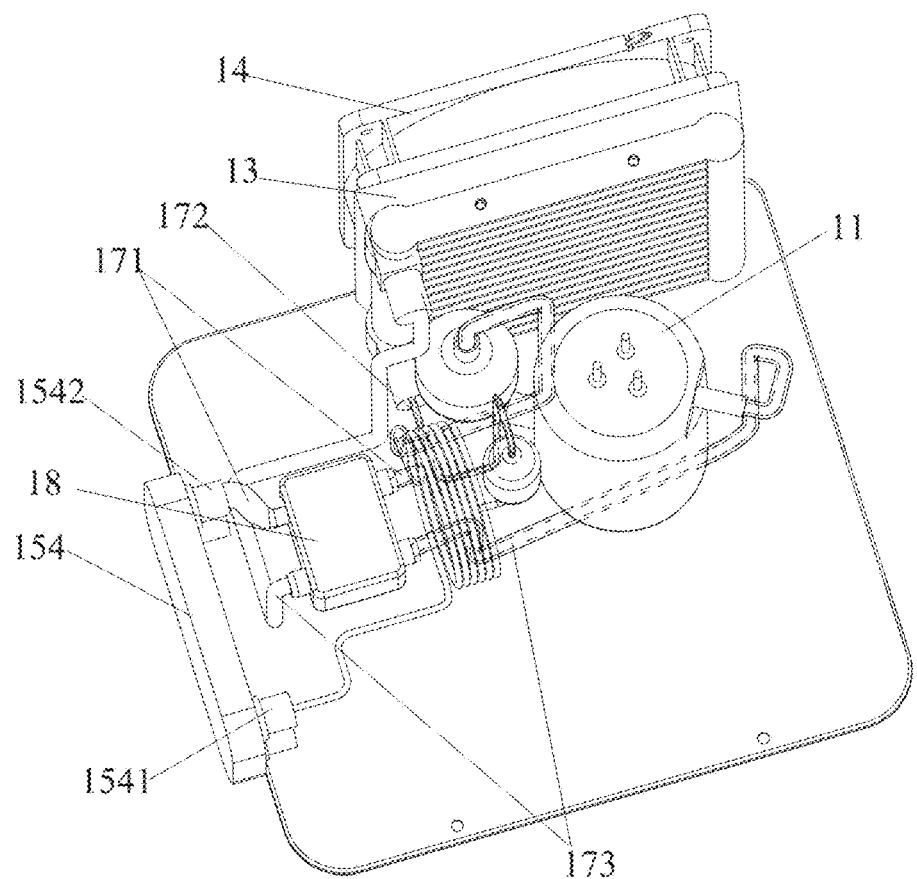
FIG. 23 is a first partial schematic structural diagram of a portable system for cold therapy with optional heat and compression therapy in a manner of the heat exchanger being a third cooling plate manner.
Figure 24:
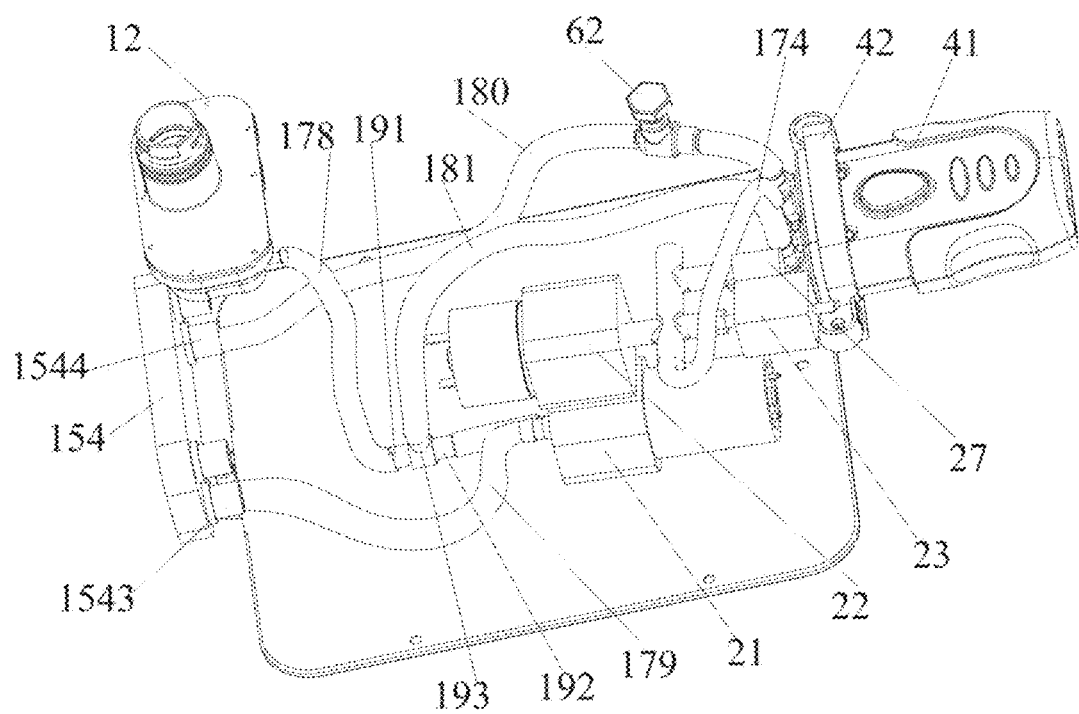
FIG. 24 is a second partial schematic structural diagram of a portable system for cold therapy with optional heat and compression therapy in a manner of the heat exchanger being a third cooling plate manner.
Figure 25:
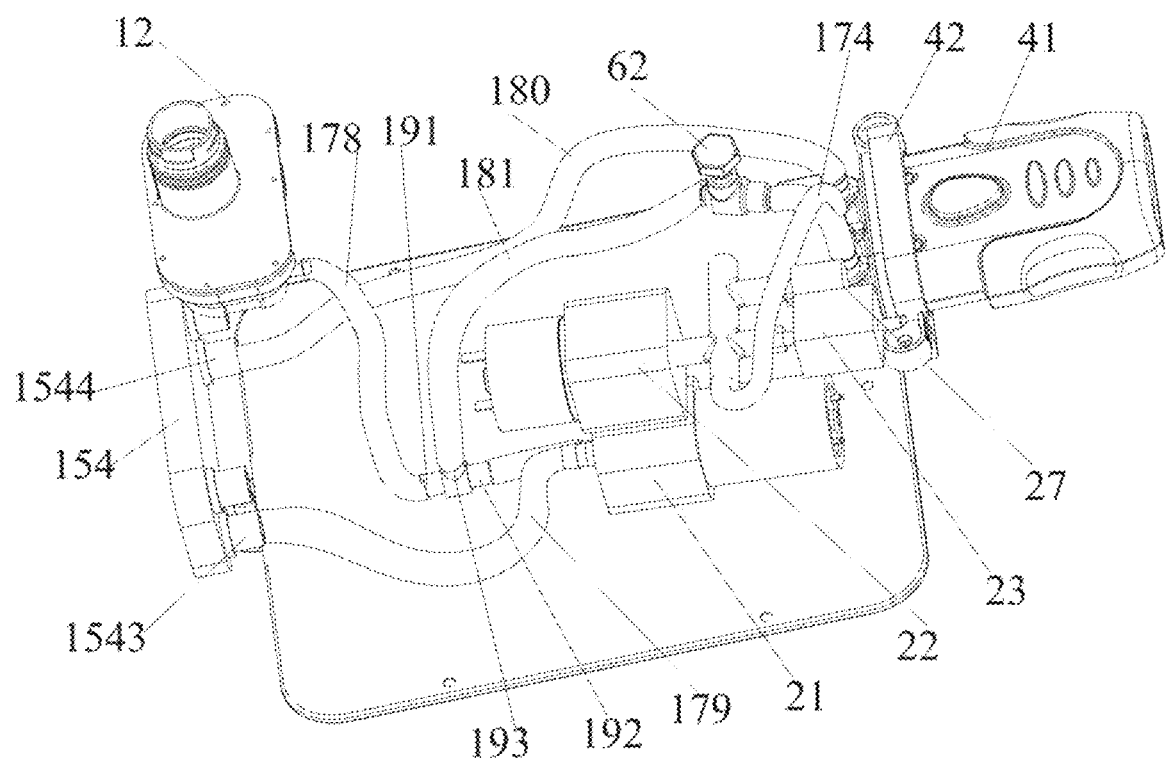
FIG. 25 is a third partial schematic structural diagram of a portable system for cold therapy with optional heat and compression therapy in a manner of the heat exchanger being a third cooling plate manner.
Figure 26:
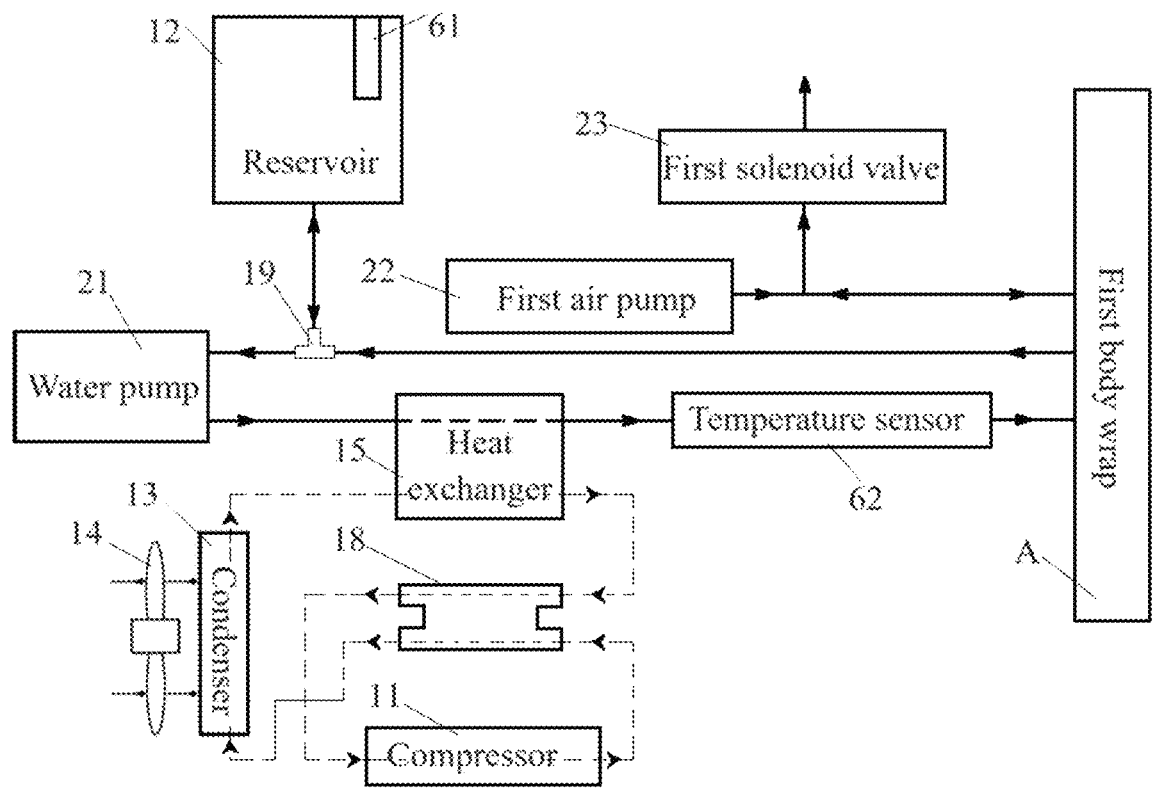
FIG. 26 is a first structural block diagram of a portable device for cold therapy with optional heat and compression therapy in a manner of the heat exchanger being a third cooling plate manner.
Figure 27:
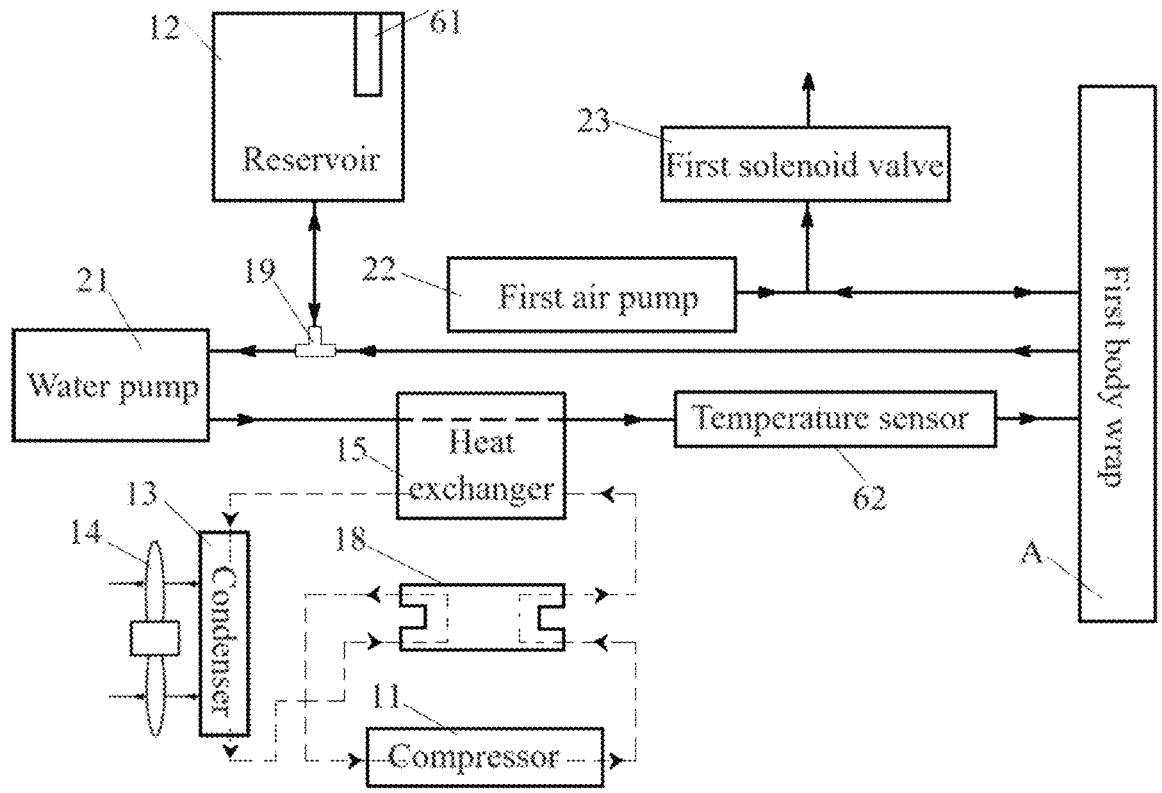
FIG. 27 is a second structural block diagram of a portable device for cold therapy with optional heat and compression therapy in a manner of the heat exchanger being a third cooling plate manner.

In one embodiment, referring to FIG. 23 to FIG. 25, the heat exchanger 15 comprises a third cooling plate 154; wherein the third cooling plate 154 is provided with a third air inlet of the third cooling plate 1541, a third air outlet of the third cooling plate 1542, a fourth liquid inlet of the third cooling plate 1543, and a fourth liquid outlet of the third cooling plate 1544; wherein the third air outlet of the third cooling plate 1542 is connected to the first tube 171, and the third air inlet of the third cooling plate 1541 is connected to the second tube 172; the fourth liquid inlet of the third cooling plate 1543 is connected to the first liquid outlet of the reservoir 122, the fourth liquid outlet of the third cooling plate 1544 is connected to a third liquid inlet A1 of the first body wrap A, a third liquid outlet A2 of the first body wrap A is connected to the first liquid outlet of the reservoir 122 and the fourth liquid inlet of the third cooling plate 1543.

It should be noted that the third cooling plate 154 includes a brazed plate heat exchanger. The liquid in the reservoir 12 flows into the fourth liquid inlet of the third cooling plate 1543 through the first liquid outlet of the reservoir 122, and the liquid flows into the first body wrap A through the fourth liquid outlet of the third cooling plate 1544 after being cooled in the brazed plate heat exchanger.

It should be noted that the refrigerant enters the third cooling plate 154 through the second tube 172 and the third air inlet of the third cooling plate 1541, and returns to the compressor 11 through the third air outlet of the third cooling plate 1542 and the first tube 171, so as to cool the third cooling plate 154 and exchange heat with the liquid in the third cooling plate 154, so as to reduce the temperature of the liquid.

In one embodiment, referring to FIG. 24 and FIG. 25, further comprising a three-way connector 19, wherein the three-way connector 19 comprises a first connector 191, a second connector 192, and a third connector 193; wherein the first connector 191 is connected to the first liquid outlet of the reservoir 122, the second connector 192 is connected to the fourth liquid inlet of the third cooling plate 1543, the third connector 193 is connected to the third liquid outlet A2.

In one embodiment, referring to FIG. 24 and FIG. 25, the first liquid outlet of the reservoir 122 is connected to the first connector 191 through a fifth tube 178, the fourth liquid inlet of the third cooling plate 1543 is connected to the second connector 192 through a sixth tube 179, the fourth liquid outlet of the third cooling plate 1544 is connected to the third liquid inlet A1 through a seventh tube 180, the third liquid outlet A2 is connected to the third connector 193 through a eighth tube 181; wherein the sixth tube 179 is provided with a water pump 21, and the water pump 21 is electrically connected to the control assembly; and wherein, in response to the water pump 21 working, the liquid in the reservoir 12 flows into the third cooling plate 154 through the fifth tube 178 and the sixth tube 179, and then flows into the first body wrap A through the seventh tube 180; the liquid in the first body wrap A flows into the third cooling plate 154 through the eighth tube 181 and the sixth tube 179, and then flows into the first body wrap A again through the seventh tube 180; in response to the water pump 21 stopped working, the liquid in the first body wrap A flows back to the reservoir 12 through the eighth tube 181 and the fifth tube 178.

It should be noted that when the water pump 21 is closed, due to the high pressure in the first body wrap A, the liquid in the first body wrap A will flow into the reservoir 12 through the eighth tube 181 and the fifth tube 178.

In one embodiment, the reservoir is further provided with a liquid level detector 61 inside, the seventh tube 180 (referring to FIG. 24) or the eighth tube 181 (referring to FIG. 25) is provided with a temperature sensor 62, and the liquid level detector 61 and the temperature sensor 62 are both electrically connected to the control assembly.

It should be noted that the liquid level detector 61 is placed in the reservoir 12 for detecting a height of a liquid position. The temperature sensor 62 is placed on the seventh tube 180 or the seventh tube 180 for detecting temperature of the liquid flows into the first body wrap A or flows out the first body wrap A, to control the temperature by means of the control assembly to achieve a suitable cold compression effect.

In one embodiment, the second tube 172 comprises a throttle device, and the throttle device is placed between the heat exchanger 15 and the condenser 13; and wherein the condenser 13 comprises a heat conduction tube, and the heat conduction tube has one end extending out of the condenser 13 to be connected to the throttle device and another end extending out of the condenser 13 to be connected to the compressor 11.

It should be noted that the second tube 172 includes a second tube connecting section extending out of the heat exchanger 15 to connect the condenser 13, and a condenser section. The throttle device is placed on the second tube connecting section extending out of the heat exchanger 15 to connect the condenser 13. The throttle device may be a capillary tube section, the second tube connecting section extends out of the heat exchanger 15 with a tendency of reduced tube diameter to form the capillary tube section. Preferably, the diameter is reduced to 3-6 times the diameter of the original tube (i.e., the second tube connecting section). The throttle device may also be a throttle valve or other throttle step-down device.

It should be noted that, after the refrigerant liquid passes through the capillary tube section with a small diameter, a flowing speed of the refrigerant liquid becomes slow due to a small sectional area of the capillary tube section, so that pressure of the refrigerant liquid is reduced, and meanwhile, the temperature of the refrigerant liquid is reduced. At this point, high-temperature and high-pressure refrigerant liquid just output from the condenser 13 is able to be depressurized through the capillary tube section.

It should be noted that the heat conduction tube includes a copper tube. High temperature and high-pressure refrigerant gas enters the condenser section, and the condenser section is provided with a copper tube. Heat of the refrigerant gas is absorbed and gradually dissipated into surrounding environment by using the copper tube. Meanwhile, the working surface of the fan 14 faces a position of the copper tube in the condenser 13, further makes the refrigerant cooling liquid. The refrigerant liquid subjected to heat dissipation through the copper tube and the fan 14 is conveyed back to the compressor 11 through the third tube 173.

In one embodiment, further comprising a first air pump 22, a first solenoid valve 23, and a first air tube 174; wherein: the first air pump 22 is connected to the first body wrap A through the first air tube 174, and the first solenoid valve 23 is arranged on the first air tube 174; the first air pump 22 and the first solenoid valve 23 are both electrically connected to the control assembly; and the first body wrap A is configured to be inflated by the first air pump 22, and the first body wrap A is configured to be deflated by the first solenoid valve 23.

It should be noted that, referring to FIG. 24 and FIG. 25, the air entering the first air tube 174 is pressurized by the first air pump 22 to be conveyed into the first body wrap A, so that the first body wrap A is inflated. In addition, the first solenoid valve 23 is a two-way solenoid valve, the first body wrap A is deflated by the first solenoid valve 23. On the one hand, the first body wrap A is expanded by inflation, allowing the first body wrap A to conform more closely to therapy areas, thereby enhancing the therapy effect of the cold therapy with optional compression therapy. On the other hand, the combination of inflation and deflation allows the first body wrap A to provide medical effects such as massage and compression.

In one embodiment, the air tube 168 is further provided with a pressure relief valve 27 and a pressure sensor 63, and the pressure sensor 63 is electrically connected to the control assembly.

It should be noted that, when the pressure sensor 63 detects excessive pressure in the trachea, the first air pump 22 can be controlled to close and the first solenoid valve 23 can be opened to deflate the first body wrap A. When the first air pump 22 or the first solenoid valve 23 fails, the air can be discharged through the pressure relief valve 27.

In one embodiment, further comprising a housing, a bracket 31, and a connector 41, wherein the housing comprises a bottom shell 32, an upper shell 33 and a surface cover 34; and wherein: the bracket 31 is embedded in the housing, and the reservoir 12 is placed on the bracket 31; an avoidance portion is displayed on the bracket 31, wherein the condenser 13 is embedded in the avoidance portion; an exterior side of the bottom shell is provided with a first groove 321, wherein the connector 41 has one end inserted into the first groove 321 and respectively connected to the seventh tube 180, the eighth tube 181, and the first air tube 174, and has another end configured to be connected to a plurality of tubes, enabling the seventh tube 180, the eighth tube 181 and the first air tube 174 to be respectively connected to the first body wrap A.

It should be noted that the bracket 31 is placed at the top of the bottom shell 32 in the housing. The bracket 31 is placed on a side of the bottom shell 32 facing the reservoir 12.

It should be noted that a dust cover 35 is provided at a position, relative to the fan 14, on the side of the housing to prevent dust and dirt from entering the interior of the fan 14.

It should be noted that a connector base 42 is placed at the first groove 321, and the connector base 42 is configured to detachably connect the connector 41 to the bottom shell 32.

In one embodiment, the control assembly includes a main control board 51, a display screen 52, and a battery 53. The display screen 52 and the battery 53 are both electrically connected to the main control board 51. The display screen 52 is placed on the surface cover 34. An exterior side of the bottom shell 32 facing the bracket 31 is recessed to form a second groove 322, and the battery 53 is placed in the second groove 322. The battery includes a storage battery.

It should be noted that the main control board 51 is controlled through the display screen 52, working temperature of the first body wrap A is able to be set, air pressure values of the first body wrap A is able to be set, and the pressing effect is achieved by adjusting the inflation and deflation.

It should be noted that the battery 53 is rechargeable, which is convenient in the absence of alternating current. For example, the device in the present disclosure is also able to work normally when outdoors, which is convenient for users to use. Furthermore, the battery 53 is able to be detached from the second groove 322, which is convenient for charging and storage.

In some examples, referring to FIG. 26, FIG. 27, FIG. 30, FIG. 31, the present disclosure provides a portable device for cold therapy with optional heat and compression therapy M including the portable system for cold therapy with optional heat and compression therapy and the first body wrap A. The present disclosure provides a portable device for cold therapy with optional heat and compression therapy M including the portable system for cold therapy with optional heat and compression therapy including a cooling mechanism, a reservoir 12, and a control assembly; wherein the cooling mechanism comprises a compressor 11, a condenser 13, a fan 14, a heat exchanger 15, and the control assembly is electrically connected to the compressor 11, the condenser 13, the fan 14, respectively; and wherein: the compressor 11, the condenser 13, the fan 14, and the heat exchanger 15 are placed outside the reservoir 12, respectively; the compressor 11 has an air inlet connected to the heat exchanger 15 through a first tube 171; the heat exchanger 15 is connected to the condenser 13 through a second tube 172; the condenser 13 is connected to an air outlet of the compressor 11 through a third tube 173; the first tube 171 and the second tube 172 are connected by fluid, and the second tube 172 and the third tube 173 are connected by fluid, enabling refrigerant gas in the compressor 11 to pass through the condenser 13 first and then through the heat exchanger 15 to achieve a cooling effect; the fan 14 has a working surface facing the condenser 13.

The reservoir 12 comprises a first liquid outlet of the reservoir 122, wherein the liquid in the reservoir 12 flows into the heat exchanger 15 first through the first liquid outlet of the reservoir 122 and then flows into the first body wrap A; the liquid in the first body wrap A can flow into the heat exchanger 15 first and then flow into the first body wrap A again, or the liquid in the first body wrap A can flow back to the reservoir 12, further comprising a heating mechanism, wherein the heating mechanism is electrically connected to the control assembly.

It should be noted that the compressor 11, the condenser 13, the fan 14 and the heat exchanger 15 can all be one or more. A plurality of the compressors 11 are arranged in series. A plurality of the condenser 13 are arranged in series, each working face of the fan 14 is toward the condenser 13. A plurality of the heat exchangers 15 are arranged in series.

In one embodiment, referring to FIG. 20, the heating mechanism comprises a four-way valve 18, wherein the compressor 11 is connected to the four-way valve 18 and then to the heat exchanger 15 through the first tube 171, and the condenser 13 is connected to the four-way valve 18 and then to the compressor 11 through the third tube 173, and the four-way valve 18 is controlled by the control assembly to change the flow direction, enabling refrigerant in the compressor 11 to pass through the heat exchanger 15 first and then through the condenser 13 to achieve a heating effect.

In one embodiment, referring to FIG. 21, the heating mechanism comprises one or more heating sheets 161, the one or more heating sheets 161 are arranged on the outside of the heat exchanger 15.

The technical problems to be solved in the embodiments lie in insufficient cooling effect and low efficiency of the cooling mechanism.

In accordance with the portable device for cold therapy with optional heat and compression therapy M provided in the present disclosure, the advantageous effects include the following. In a first aspect, the cooling mechanism is equipped with the compressor 11, the condenser 13, the fan 14, the heat exchanger 15. High temperature and high-pressure refrigerant gas is transported from the compressor 11 to the condenser 13 through the third tube 173, at this time, the temperature of the refrigerant gas is high, and the fan is utilized to cool the refrigerant gas in the condenser 13, and the refrigerant gas is liquefied. Refrigerant liquid is transported from the condenser 13 to the heat exchanger 15 through the second tube 172. In the heat exchanger 15, the refrigerant liquid undergoes heat exchange with the liquid in the heat exchanger 15, absorbs heat from the liquid and gasifies, and the liquid temperature decreases. Refrigerant gas is transported from the heat exchanger 15 to the compressor 11 through the first tube 171, and the compressor 11 compresses the refrigerant gas. The heat exchanger 15 is arranged on the outside of the reservoir 12, the liquid in the reservoir 12 flows into the heat exchanger 15 for cooling through the first liquid outlet of the reservoir 122 and then flows into the first body wrap A. The liquid in the first body wrap A can flow into the heat exchanger 15 for cooling again, or the liquid in the first body wrap A can flow back into the reservoir 12, providing the first body wrap A with a cold compression function, and the remaining liquid in the reservoir 12 will no longer participate in the circulation, to greatly improve the cooling efficiency, and reduce the power consumption. Referring to FIG. 30, under the condition of the ambient temperature of 25-28° C., with an area of 1 m$^2$ of the first body wrap A, a cooling rate is such that the surface temperature of the first body wrap A reaches 5° C. within about 5 minutes, a cooling power is about 75 watts, and the achieved cooling capacity is about 250 watts. The system exhibits excellent cooling effects, high efficiency, stability, and low power consumption. In a second aspect, further comprising a heating mechanism, the heating mechanism comprises a four-way valve 18 or one or more heating sheets 161, the control assembly controls the four-way valve 18 to change the flow direction or control the heating sheet heating 161, to increase the temperature of the liquid in the heat exchanger 15, the liquid with increased temperature flows into the first body wrap A through the third liquid inlet A1, providing the first body wrap A with a hot compression function. Referring to FIG. 31, under the condition of the ambient temperature of 25-28° C., with an area of 1 m$^2$ of the first body wrap A, a heating rate is such that the surface temperature of the first body wrap A reaches 43° C. within about 6 minutes, a heating power is about 75-150 watts, and the achieved heating capacity is about 75-150 watts. The device exhibits excellent heating effects, high efficiency, and stability. In a third aspect, the first air pump 22 and the first solenoid valve 23 are provided to inflate the first body wrap A, allowing the first body wrap A to conform more closely to therapy areas. This enhances the therapy effect of the cold therapy with optional heat and compression therapy. Additionally, the combination of inflation and deflation allows the first body wrap A to provide medical effects such as massage and compression. The cooling and heating mechanisms are simultaneously incorporated into the portable device for cold therapy with optional heat and compression therapy, provided in the present disclosure. The device has a compact, small, and lightweight structure, facilitating convenient portability. The device is versatile, offering capabilities for cold compression, hot compression, and/or massage, enhancing the user experience.

In one embodiment, shunt tubes are provided in the first body wrap A.

In some examples, referring to FIG. 1 to FIG. 19, the present disclosure provides a portable device M for cold therapy with optional heat and compression therapy including the portable system for cold therapy with optional heat and compression therapy as described in any one of the embodiments. The portable device M for cold therapy with optional heat and compression therapy further includes a first body wrap A, and the first body wrap A is connected to the reservoir 12 through the first liquid outlet of the reservoir 122 and the first liquid inlet of the reservoir 121, respectively.

In accordance with the portable device M for cold therapy with optional heat and compression therapy provided in the present disclosure, the advantageous effects include the following. In some examples, the body wrap cooling mechanism is equipped with the compressor 11, the condenser 13, the fan 14, and the heat exchanger 15. Liquid gas is transported from the compressor 11 to the heat exchanger 15 through the first tube 1711. In the heat exchanger 15, the liquid gas undergoes heat exchange with the liquid in the reservoir 12, absorbs heat from the liquid and gasifies, and the liquid temperature decreases. The gasified gas is then transported from the heat exchanger 15 to the condenser 13 through the second tube 172. At this point, the temperature of the gasified gas transported from the heat exchanger 15 to the condenser 13 is relatively high, and the fan 14 is utilized to cool the gasified gas in the condenser 13. The cooled gas is then transported from the condenser 13 to the compressor 11 through the third tube 173, and the compressor 11 compresses and liquefies the gas. This process circulates to cool the liquid in the reservoir 12. A cooling rate is such that the liquid decreases from room temperature to 5° C. within about 10 minutes. A cooling power is about 75 watts, and the achieved cooling capacity is about 150 watts. The system exhibits excellent cooling effects, high efficiency, stability, and low power consumption. The liquid with decreased temperature flows into the first body wrap A through the liquid inlet of the first body wrap, providing the body wrap with a cold compression function. In some examples, the air pumps and the solenoid valves are provided to inflate the body wrap, allowing the body wrap to conform more closely to the therapy area. This enhances the therapy effect of the cold therapy with optional heat and compression therapy. Additionally, the combination of inflation and deflation allows the body wrap to provide medical effects such as massage and compression. In some examples, the compressor 11, condenser 13, and fan 14 are paused by the control assembly. The heating tube 16 is activated by the control assembly to increase the temperature of the liquid in the reservoir 12. A heating rate is such that the liquid reaches 43° C. from room temperature within about 6 minutes. The heating power is about 150 watts, and the achieved heating capacity is about 150 watts. The device exhibits excellent heating effects, high efficiency, and stability. The liquid with increased temperature flows into the first body wrap A through the liquid inlet of the first body wrap, providing the body wrap with a hot compression function. The cooling and heating mechanisms are simultaneously incorporated into the portable device M for cold therapy with optional heat and compression therapy provided in the present disclosure. The overall volume of the device is approximately 0.014 m³, with a mass of about 3.8 kg, which has a compact, small, and lightweight structure, facilitating convenient portability. The device is versatile, offering capabilities for cold compression, hot compression, and/or massage, enhancing the user experience.

Furthermore, as the cooling and heating mechanisms in the present disclosure is placed inside or underneath the reservoir 12, which are able to directly or indirectly contact the liquid in the reservoir. This allows pre-cooling or pre-heating of the liquid, thereby enabling immediate use when the user requires therapy.

In one embodiment, the portable device M for cold therapy with optional heat and compression therapy further includes a second body wrap B and a third body wrap C. The second air pump 24 is connected to the second body wrap B through the second air tube 175 and to the third body wrap C through the third air tube 176.

Figure 19:
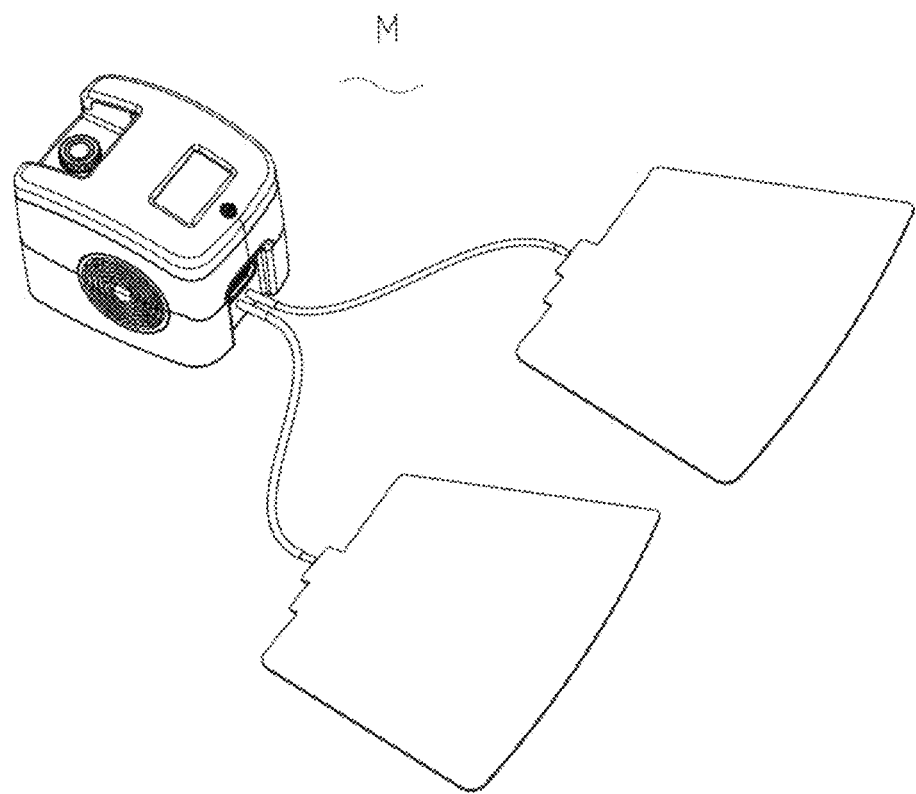
FIG. 19 is a second schematic structural diagram of a portable device for cold therapy with optional heat and compression therapy according to an embodiment of the present disclosure.

It should be noted that, referring to FIG. 19, when a user only needs the air pressure function, the second body wrap B is able to be connected to the second air pump 24 through the second air tube 175 and the third body wrap C is able to be connected to the second air pump 24 through the third air tube 176. The combination of inflation and deflation allows the second body wrap B and the third body wrap C to provide medical effects such as massage and compression.

In one embodiment, shunt tubes are provided in the first body wrap A.

The description of the embodiments described above enables those skilled in the art to implement or use the present disclosure. Various modifications to these embodiments will be apparent to those skilled in the art, and general principles defined herein may be implemented in other embodiments without departing from the spirit or scope of the present disclosure. Therefore, the present disclosure is not limited to the embodiments described herein but is to be accorded the widest scope consistent with the principles and novel features disclosed herein.

What is claimed is:

1. A portable system for cold therapy with optional heat and compression therapy, applied to a first body wrap, comprising a cooling mechanism, a reservoir, and a control assembly; wherein the cooling mechanism comprises a compressor, a condenser, a fan, and a heat exchanger, and the control assembly is electrically connected to the compressor and the fan, respectively; and wherein:

the compressor, the condenser, and the fan are placed outside the reservoir; the heat exchanger is placed inside or underneath the reservoir, and is in direct or indirect contact with liquid in the reservoir to cool the liquid;

the compressor has an air inlet connected to the heat exchanger through a first tube;

the heat exchanger is connected to the condenser through a second tube;

the condenser is connected to an air outlet of the compressor through a third tube;

the first tube and the second tube are connected by fluid, and the second tube and the third tube are connected by fluid, enabling refrigerant in the compressor to pass through the condenser first and then through the heat exchanger to achieve a cooling effect;

the fan has a working surface facing the condenser; and the reservoir comprises a first liquid inlet of the reservoir and a first liquid outlet of the reservoir; wherein the liquid in the reservoir flows into the first body wrap through the first liquid outlet of the reservoir, and liquid in the first body wrap flows into the reservoir through the first liquid inlet of the reservoir;

the heat exchanger comprises a first cooling plate placed inside the reservoir; wherein the first cooling plate comprises a first air inlet of the first cooling plate, a first air outlet of the first cooling plate, a second liquid inlet of the first cooling plate, and a second liquid outlet of the first cooling plate; and wherein the first air outlet of the first cooling plate is connected to the first tube, and the first air inlet of the first cooling plate is connected to the second tube; and the second liquid inlet of the first cooling plate is connected to the first liquid inlet of the reservoir through a fourth tube.

2. The portable system for cold therapy with optional heat and compression therapy according to claim 1, wherein the reservoir is further provided with a liquid level detector and a temperature sensor inside, and the liquid level detector and the temperature sensor are both electrically connected to the control assembly.

3. The portable system for cold therapy with optional heat and compression therapy according to claim 1, wherein the second tube comprises a throttle device, and the throttle device is placed between the heat exchanger and the condenser; and wherein the condenser comprises a heat conduction tube, and the heat conduction tube has one end extending out of the condenser to be connected to the throttle device and another end extending out of the condenser to be connected to the compressor.

4. The portable system for cold therapy with optional heat and compression therapy according to claim 1, further comprising a water pump, wherein the first liquid outlet of the reservoir is connected to a third liquid inlet of the first body wrap through the water pump, and the water pump is electrically connected to the control assembly; and wherein, in response to the water pump working, the liquid in the reservoir flows into the first body wrap through the first liquid outlet of the reservoir and the third liquid inlet, and the liquid in the first body wrap flows back into the reservoir through a third liquid outlet of the first body wrap and the first liquid inlet of the reservoir.

5. The portable system for cold therapy with optional heat and compression therapy according to claim 1, further comprising a four-way valve, wherein the compressor is connected to the four-way valve and then to the heat exchanger through the first tube, and the condenser is connected to the four-way valve and then to the compressor through the third tube; and wherein, the four-way valve is electrically connected to the control assembly, and the four-way valve is controlled by the control assembly to change the flow direction, enabling refrigerant in the compressor to pass through the heat exchanger first and then through the condenser to achieve a heating effect.

6. The portable system for cold therapy with optional heat and compression therapy according to claim 1, further comprising a heating mechanism, wherein the heating mechanism comprises a heating tube; and wherein the heating tube is placed inside the reservoir and is electrically connected to the control assembly.

7. The portable system for cold therapy with optional heat and compression therapy according to claim 1, further comprising a first air pump, a first solenoid valve, and a first air tube; wherein:

the first air pump is connected to the first body wrap through the first air tube, and the first solenoid valve is arranged on the first air tube;

the first air pump and the first solenoid valve are both electrically connected to the control assembly; and the first body wrap is configured to be inflated by the first air pump, and the first body wrap is configured to be deflated by the first solenoid valve.

8. The portable system for cold therapy with optional heat and compression therapy according to claim 7, further comprising a second air pump, a second solenoid valve, a third solenoid valve, a second air tube, and a third air tube; wherein:

the second air pump is connected to the second body wrap through the second air tube, and the second solenoid valve is arranged on the second air tube; the second air pump is connected to the third body wrap through the third air tube, and the third solenoid valve is arranged on the third air tube;

the second air pump, the second solenoid valve, and the third solenoid valve are all electrically connected to the control assembly; and the second body wrap and the third body wrap are configured to be inflated by the second air pump, the second body wrap is configured to be deflated by the second solenoid valve, and the third body wrap is configured to be deflated by the third solenoid valve.

9. The portable system for cold therapy with optional heat and compression therapy according to claim 8, further comprising a housing, a bracket, and a connector, wherein the housing comprises a bottom shell, an upper shell and a surface cover; and wherein:

the bracket is embedded in the housing, and the reservoir is placed on the bracket;

an avoidance portion is displayed on the bracket, wherein the condenser is embedded in the avoidance portion;

an exterior side of the bottom shell is provided with a first groove, wherein the connector has one end inserted into the first groove and respectively connected to the first liquid outlet of the reservoir, the first liquid inlet of the reservoir and the first air tube, and has another end configured to be connected to a plurality of tubes, enabling the first liquid outlet of the reservoir, the first liquid inlet of the reservoir and the first air tube to be respectively connected to the first body wrap; and the bottom shell is further provided with a first air hole and a second air hole, wherein the first air hole and the second air hole are placed below the first groove; and wherein one side of the first air hole is connected to the second air tube, one side of the second air hole is connected to the third air tube, and another side of the first air hole and another side of the second air hole are configured to be connected to tubes, enabling the second air tube to be connected to the second body wrap and the third air tube to be connected to the third body wrap.

10. The portable system for cold therapy with optional heat and compression therapy according to claim 9, wherein the control assembly further comprises a main control board, a display screen, and a battery; and wherein:

the display screen and the battery are both electrically connected to the main control board;

the display screen is placed on the surface cover; and an exterior side of the bottom shell is recessed towards the bracket to form a second groove, wherein the battery is placed in the second groove, and the battery comprises a storage battery.

11. A portable system for cold therapy with optional heat and compression therapy, applied to a first body wrap, comprising a cooling mechanism, a reservoir, and a control assembly; wherein the cooling mechanism comprises a compressor, a condenser, a fan, and a heat exchanger, and the control assembly is electrically connected to the compressor and the fan, respectively; and wherein:

the compressor, the condenser, and the fan are placed outside the reservoir; the heat exchanger is placed inside or underneath the reservoir, and is in direct or indirect contact with liquid in the reservoir to cool the liquid;

the compressor has an air inlet connected to the heat exchanger through a first tube;

the heat exchanger is connected to the condenser through a second tube;

the condenser is connected to an air outlet of the compressor through a third tube;

the first tube and the second tube are connected by fluid, and the second tube and the third tube are connected by fluid, enabling refrigerant in the compressor to pass through the condenser first and then through the heat exchanger to achieve a cooling effect;

the fan has a working surface facing the condenser;

the reservoir comprises a first liquid inlet of the reservoir and a first liquid outlet of the reservoir; wherein the liquid in the reservoir flows into the first body wrap through the first liquid outlet of the reservoir, and liquid in the first body wrap flows into the reservoir through the first liquid inlet of the reservoir;

the heat exchanger is placed underneath the reservoir, the heat exchanger comprises a second cooling plate; wherein the second cooling plate is provided with a second air inlet of the second cooling plate and a second air outlet of the second cooling plate, the second air outlet of the second cooling plate is connected to the first tube, and the second air inlet of the second cooling plate is connected to the second tube; and wherein the reservoir comprises a heat-conducting material; and the portable system further comprises a housing, a bracket, and a connector, the housing comprises a bottom shell, an upper shell and a surface cover, the bracket is embedded in the housing, and the reservoir is placed on the bracket, and an avoidance portion is displayed on the bracket, wherein the condenser is embedded in the avoidance portion.

12. The portable system for cold therapy with optional heat and compression therapy according to claim 11, wherein:

an exterior side of the bottom shell is provided with a first groove, wherein the connector has one end inserted into the first groove and respectively connected to the first liquid outlet of the reservoir, the first liquid inlet of the reservoir, and a first air tube, and has another end configured to be connected to a plurality of tubes, enabling the first liquid outlet of the reservoir, the first liquid inlet of the reservoir and the first air tube to be respectively connected to the first body wrap; and the bottom shell is further provided with a first air hole and a second air hole, wherein the first air hole and the second air hole are placed below the first groove; and wherein one side of the first air hole is connected to a second air tube, one side of the second air hole is connected to a third air tube, and another side of the first air hole and another side of the second air hole are configured to be connected to tubes, enabling the second air tube to be connected to a second body wrap and the third air tube to be connected to a third body wrap.

13. The portable system for cold therapy with optional heat and compression therapy according to claim 12, wherein the control assembly further comprises a main control board, a display screen, and a battery; and wherein:

the display screen and the battery are both electrically connected to the main control board;

the display screen is placed on the surface cover; and an exterior side of the bottom shell is recessed towards the bracket to form a second groove, wherein the battery is placed in the second groove, and the battery comprises a storage battery.

14. The portable system for cold therapy with optional heat and compression therapy according to claim 11, further comprising a four-way valve, wherein the compressor is connected to the four-way valve and then to the heat exchanger through the first tube, and the condenser is connected to the four-way valve and then to the compressor through the third tube; and wherein, the four-way valve is electrically connected to the control assembly, and the four-way valve is controlled by the control assembly to change the flow direction, enabling refrigerant in the compressor to pass through the heat exchanger first and then through the condenser to achieve a heating effect.

15. A portable system for cold therapy with optional heat and compression therapy, applied to a first body wrap, comprising a cooling mechanism, a reservoir, and a control assembly; wherein the cooling mechanism comprises a compressor, a condenser, a fan, and a heat exchanger, and the control assembly is electrically connected to the compressor, and the fan, respectively; and wherein:

the compressor, the condenser, the fan, and the heat exchanger are placed outside the reservoir, respectively;

the compressor has an air inlet connected to the heat exchanger through a first tube;

the heat exchanger is connected to the condenser through a second tube;

the condenser is connected to an air outlet of the compressor through a third tube;

the first tube and the second tube are connected by fluid, and the second tube and the third tube are connected by fluid, enabling refrigerant in the compressor to pass through the condenser first and then through the heat exchanger to achieve a cooling effect;

the fan has a working surface facing the condenser; and the reservoir comprises a first liquid outlet of the reservoir, wherein the liquid in the reservoir flows into the heat exchanger first through the first liquid outlet of the reservoir and then flows into the first body wrap; the liquid in the first body wrap can flow into the heat exchanger first and then flow into the first body wrap again, or the liquid in the first body wrap can flow back to the reservoir;

further comprising a heating mechanism, wherein the heating mechanism is electrically connected to the control assembly; and the heating mechanism comprises one or more heating sheets; the one or more heating sheets are arranged on the outside of the heat exchanger;

wherein the heat exchanger comprises a third cooling plate; wherein the third cooling plate is provided with a third air inlet of the third cooling plate, a third air outlet of the third cooling plate, a fourth liquid inlet of the third cooling plate, and a fourth liquid outlet of the third cooling plate;

wherein the third air outlet of the third cooling plate is connected to the first tube, and the third air inlet of the third cooling plate is connected to the second tube; the fourth liquid inlet of the third cooling plate is connected to the first liquid outlet of the reservoir, the fourth liquid outlet of the third cooling plate is connected to a third liquid inlet of the first body wrap, a third liquid outlet of the first body wrap is connected to the first liquid outlet of the reservoir and the fourth liquid inlet of the third cooling plate.

16. The portable system for cold therapy with optional heat and compression therapy according to claim 15, further comprising a insulation device, the insulation device is arranged on the outside of the heating sheet.

17. The portable system for cold therapy with optional heat and compression therapy according to claim 15, further comprising a three-way connector, wherein the three-way connector comprises a first connector, a second connector, and a third connector;

wherein the first connector is connected to the first liquid outlet of the reservoir, the second connector is connected to the fourth liquid inlet of the third cooling plate, the third connector is connected to the third liquid outlet.

18. The portable system for cold therapy with optional heat and compression therapy according to claim 17, wherein the first liquid outlet of the reservoir is connected to the first connector through a fifth tube, the fourth liquid inlet of the third cooling plate is connected to the second connector through a sixth tube, the fourth liquid outlet of the third cooling plate is connected to the third liquid inlet through a seventh tube, the third liquid outlet is connected to the third connector through a eighth tube;
  wherein the sixth tube is provided with a water pump, and the water pump is electrically connected to the control assembly; and wherein,
  in response to the water pump working, the liquid in the reservoir flows into the third cooling plate through the fifth tube and the sixth tube, and then flows into the first body wrap through the seventh tube; the liquid in the first body wrap flows into the third cooling plate through the eighth tube and the sixth tube, and then flows into the first body wrap again through the seventh tube;
  in response to the water pump stopped working, the liquid in the first body wrap flows back to the reservoir through the eighth tube and the fifth tube.

19. The portable system for cold therapy with optional heat and compression therapy according to claim 18, wherein the reservoir is further provided with a liquid level detector inside, the seventh tube or the eighth tube is provided with a temperature sensor, and the liquid level detector and the temperature sensor are both electrically connected to the control assembly.

20. The portable system for cold therapy with optional heat and compression therapy according to claim 15, wherein the second tube comprises a throttle device, and the throttle device is placed between the heat exchanger and the condenser; and wherein the condenser comprises a heat conduction tube, and the heat conduction tube has one end extending out of the condenser to be connected to the throttle device and another end extending out of the condenser to be connected to the compressor.

21. The portable system for cold therapy with optional heat and compression therapy according to claim 18, further comprising a first air pump, a first solenoid valve, and a first air tube; wherein:
  the first air pump is connected to the first body wrap through the first air tube, and the first solenoid valve is arranged on the first air tube;
  the first air pump and the first solenoid valve are both electrically connected to the control assembly; and
  the first body wrap is configured to be inflated by the first air pump, and the first body wrap is configured to be deflated by the first solenoid valve.

22. The portable system for cold therapy with optional heat and compression therapy according to claim 21, further comprising a housing, a bracket, and a connector, wherein the housing comprises a bottom shell, an upper shell and a surface cover; and wherein:
  the bracket is embedded in the housing, and the reservoir is placed on the bracket;
  an avoidance portion is displayed on the bracket, wherein the condenser is embedded in the avoidance portion;
  an exterior side of the bottom shell is provided with a first groove, wherein the connector has one end inserted into the first groove and respectively connected to the seventh tube, the eighth tube, and the first air tube, and has another end configured to be connected to a plurality of tubes, enabling the seventh tube, the eighth tube and the first air tube to be respectively connected to the first body wrap.

23. The portable system for cold therapy with optional heat and compression therapy according to claim 22, wherein the control assembly further comprises a main control board, a display screen, and a battery; and wherein:
  the display screen and the battery are both electrically connected to the main control board;
  the display screen is placed on the surface cover; and
  an exterior side of the bottom shell is recessed towards the bracket to form a second groove, wherein the battery is placed in the second groove, and the battery comprises a storage battery.

24. A portable device for cold therapy with optional heat and compression therapy, comprising a portable system for cold therapy with optional heat and compression therapy and a first body wrap; wherein the portable system for cold therapy with optional heat and compression therapy comprises a cooling mechanism, a reservoir, and a control assembly; wherein the cooling mechanism comprises a compressor, a condenser, a fan, and a heat exchanger, and the control assembly is electrically connected to the compressor and the fan, respectively; and wherein:
  the compressor, the condenser, the fan, and the heat exchanger are placed outside the reservoir, respectively;
  the compressor has an air inlet connected to the heat exchanger through a first tube;
  the heat exchanger is connected to the condenser through a second tube;
  the condenser is connected to an air outlet of the compressor through a third tube;
  the first tube and the second tube are connected by fluid, and the second tube and the third tube are connected by fluid, enabling refrigerant in the compressor to pass through the condenser first and then through the heat exchanger to achieve a cooling effect;
  the fan has a working surface facing the condenser; and
  the reservoir comprises a first liquid outlet of the reservoir, wherein the liquid in the reservoir flows into the heat exchanger first through the first liquid outlet of the reservoir and then flows into the first body wrap; the liquid in the first body wrap can flow into the heat exchanger first and then flow into the first body wrap again, or the liquid in the first body wrap can flow back to the reservoir;
  further comprising a heating mechanism, wherein the heating mechanism is electrically connected to the control assembly; and
  the heating mechanism comprises a four-way valve; wherein the compressor is connected to the four-way valve and then to the heat exchanger through the first tube, and the condenser is connected to the four-way valve and then to the compressor through the third tube; and the four-way valve is controlled by the control assembly to change the flow direction, enabling refrigerant in the compressor to pass through the heat exchanger first and then through the condenser to achieve a heating effect.

* * * * *